US009170245B2

(12) United States Patent
Landgrebe et al.

(10) Patent No.: US 9,170,245 B2
(45) Date of Patent: Oct. 27, 2015

(54) CHEMICAL INDICATOR COMPOSITION, INDICATORS AND METHODS

(75) Inventors: Kevin D. Landgrebe, Woodbury, MN (US); David M. Read, White Bear Lake, MN (US); Steven S. Kirckof, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 586 days.

(21) Appl. No.: 13/142,752

(22) PCT Filed: Dec. 30, 2009

(86) PCT No.: PCT/US2009/069815
§ 371 (c)(1),
(2), (4) Date: Jun. 29, 2011

(87) PCT Pub. No.: WO2010/078422
PCT Pub. Date: Jul. 8, 2010

(65) Prior Publication Data
US 2011/0275159 A1 Nov. 10, 2011

Related U.S. Application Data

(60) Provisional application No. 61/141,912, filed on Dec. 31, 2008, provisional application No. 61/231,870, filed on Aug. 6, 2009.

(51) Int. Cl.
*G01N 21/78* (2006.01)
*G01N 31/22* (2006.01)
(Continued)

(52) U.S. Cl.
CPC ............... *G01N 31/226* (2013.01); *A61L 2/28* (2013.01); *C09D 11/50* (2013.01); *G01N 21/81* (2013.01); *A61L 2/07* (2013.01); *Y10T 428/31996* (2015.04)

(58) Field of Classification Search
USPC ............ 106/31.13, 31.16; 116/206–207, 216; 252/408.1; 374/161–162; 422/11, 26, 422/402, 420, 425, 430; 436/1–2, 164, 166, 436/169
See application file for complete search history.

(56) References Cited

U.S. PATENT DOCUMENTS 1,844,199 A * 2/1932 Bicknell et al. ............... 346/134
2,118,144 A   8/1932 Berman et al.
(Continued)

FOREIGN PATENT DOCUMENTS

CN   13/142752   12/2009
GB   1132334    10/1968
(Continued)

OTHER PUBLICATIONS

Derwent Abstract for JP 02-211162 1990, 1 page.*
(Continued)

*Primary Examiner* — Arlen Soderquist

(57) ABSTRACT

A chemical indicator composition comprising a bismuth (III) compound selected from the group consisting of bismuth (III) oxide and a bismuth (III) compound comprising at least one organic group which includes 2 to 20 carbon atoms; elemental sulfur; and a compound which makes the composition alkaline when exposed to water vapor at an elevated temperature; a chemical indicator composition comprising a bismuth (III) compound; elemental sulfur; a compound which makes the composition alkaline when exposed to water vapor at an elevated temperature; and at least one acid other than any acid present in the bismuth (III) compound; a chemical indicator comprising a substrate and the composition coated on at least a portion of a major surface of the substrate; methods of making the chemical indicator; and methods of using the chemical indicator are disclosed.

19 Claims, 8 Drawing Sheets

(51) Int. Cl.
*A61L 2/28* (2006.01)
*C09D 11/50* (2014.01)
*G01N 21/81* (2006.01)
*A61L 2/07* (2006.01)

(56) References Cited

U.S. PATENT DOCUMENTS

| | | | |
|---|---|---|---|
| 1,924,793 A * | 8/1933 | Laske | 106/287.18 |
| 2,625,494 A * | 1/1953 | Morrison | 503/202 |
| 2,889,799 A * | 6/1959 | Korpman | 116/207 |
| 3,313,266 A * | 4/1967 | Kelson | 116/207 |
| 3,360,338 A | 12/1967 | Edenbaum | |
| 3,360,339 A | 12/1967 | Edenbaum | |
| 3,386,807 A | 6/1968 | Edenbaum | |
| 3,471,422 A | 10/1969 | Edlein et al. | |
| 3,616,898 A * | 11/1971 | Massie | 206/216 |
| 4,121,011 A * | 10/1978 | Glover et al. | 428/347 |
| 4,424,990 A * | 1/1984 | White et al. | 285/381.2 |
| 4,514,361 A | 4/1985 | Hirsch | |
| 4,579,715 A | 4/1986 | Bruso | |
| 5,057,433 A | 10/1991 | Douglas | |
| 5,064,576 A | 11/1991 | Suto | |
| 5,855,655 A * | 1/1999 | Nohr et al. | 106/31.27 |
| 5,916,816 A | 6/1999 | Read | |
| 6,168,655 B1 * | 1/2001 | Nohr et al. | 106/31.58 |
| 6,485,978 B1 * | 11/2002 | Kirckof et al. | 436/1 |
| 6,488,890 B1 * | 12/2002 | Kirckof | 422/403 |
| 6,884,394 B1 * | 4/2005 | Hehenberger et al. | 422/404 |
| 7,718,433 B2 * | 5/2010 | Stecklein et al. | 436/10 |
| 2011/0312096 A1 * | 12/2011 | Whitman et al. | 436/1 |

FOREIGN PATENT DOCUMENTS

| | | | |
|---|---|---|---|
| JP | 02211162 | | 8/1990 |
| JP | 04364174 | | 12/1992 |
| JP | WO 98/13431 | | 4/1998 |
| JP | 11-80703 | | 3/1999 |
| JP | 2002322315 | | 11/2002 |
| JP | 2002323451 | | 11/2002 |
| JP | 2004016680 | | 1/2004 |
| JP | 2004-222957 | | 8/2004 |
| JP | 2005178871 | | 7/2005 |
| JP | 2006-3274 | * | 1/2006 |
| JP | 2006104346 | | 4/2006 |
| JP | WO 2009/069815 | | 12/2009 |
| JP | WO 2010/078422 | | 7/2010 |
| JP | 2006-1206 | * | 1/2013 |
| JP | 2004-317433 | * | 11/2013 |
| JP | 2005-329983 | * | 12/2013 |

OTHER PUBLICATIONS

ANSI/AAMI/ISO 11140-5:2007, Sterilization of health care products—Chemical indicators—Part 5: Class 2 indicators for air removal test sheets and packs, 2nd ed.

* cited by examiner

CHEMICAL INDICATOR COMPOSITION, INDICATORS AND METHODS

CROSS REFERENCE TO RELATED APPLICATION

This application is the National Stage filing under 35 U.S.C. 371 of International Application No. PCT/US2009/069815 filed Dec. 30, 2009, which claims the benefit of U.S. Provisional Patent Application No. 61/141,912, filed Dec. 31, 2008 and U.S. Provisional Patent Application No. 61/231,870, filed Aug. 6, 2009, which are incorporated herein by reference.

BACKGROUND

A variety of products and articles, including, for example, medical instruments, devices, and equipment, must be sterilized prior to use to prevent bio-contamination of a wound site, a sample, an organism, or the like. A number of sterilization processes are used which involve contacting the product or article with a sterilant. Examples of such sterilants include steam, ethylene oxide, hydrogen peroxide, and the like. Steam sterilization is widely used, at least in part because multiple batches of articles can be subjected to sterilization conditions during a 24 hour period using a single steam sterilizer.

Monitoring for conditions sufficient for sterilization is generally carried out by placing an appropriate sterilization indicator along with the product and/or article to be sterilized within a sterilization chamber. A variety of sterilization indicators, including chemical and biological indicators, are known and used for this purpose. Chemical indicators offer an advantage in that they can be read immediately at the end of a sterilization process. Steam sterilization indicator compositions that have been used include a polyvalent metal compound, such as lead carbonate, and sulfur. Such indicators turn to brown or black when their color is fully developed by a steam sterilization condition.

Because of environmental concerns, lead compounds have been and continue to be replaced by other polyvalent metal compounds. In one example, bismuth has been proposed to replace lead in certain steam sterilization indicator compositions as described in U.S. Pat. No. 5,916,816 (Read) wherein, for example, bismuth subcarbonate was used.

Accordingly, there is a continuing need for lead-free chemical indicators which can indicate that a steam sterilization process condition has been met.

SUMMARY OF THE INVENTION

The present invention provides a chemical indicator composition, a chemical indicator including the composition, a method of determining the effectiveness of a sterilization process using the indicator, and a method of making a chemical indicator having a targeted change in optical density when exposed to a steam sterilization process condition.

In one embodiment, there is provided a chemical indicator composition comprising:
 a) a bismuth (III) compound selected from the group consisting of bismuth (III) oxide and a bismuth (III) compound comprising at least one organic group which includes 2 to 20 carbon atoms;
 b) elemental sulfur; and
 c) a compound which makes the composition alkaline when exposed to water vapor at an elevated temperature.

In another embodiment, there is provided a chemical indicator comprising:
 a substrate and a chemical indicator composition coated on at least a portion of a major surface of the substrate, the composition comprising:
 a) a bismuth (III) compound selected from the group consisting of bismuth (III) oxide and a bismuth (III) compound comprising at least one organic group which includes 2 to 20 carbon atoms;
 b) elemental sulfur; and
 c) a compound which makes the composition alkaline when exposed to water vapor at an elevated temperature.

In another embodiment, there is provided a chemical indicator composition comprising:
 a) a bismuth (III) compound;
 b) elemental sulfur;
 c) a compound which makes the composition alkaline when exposed to water vapor at an elevated temperature; and
 d) at least one acid other than any acid present in the bismuth (III) compound.

In another embodiment, there is provided a chemical indicator comprising:
 a substrate and any one of the above chemical indicator compositions coated on at least a portion of a major surface of the substrate. Any one of the above compositions includes any one embodiment thereof described herein.

In another embodiment, there is provided a method of determining the effectiveness of a steam sterilization process, the method comprising:
 providing any one of the above chemical indicators;
 placing the chemical indicator in a steam sterilization chamber;
 exposing the chemical indicator to steam at a temperature of at least 121° C.; and
 determining an optical density of the chemical indicator.

In another embodiment, there is provided a method of making a chemical indicator having a targeted change in optical density when exposed to a steam sterilization process condition; the method comprising:
 selecting at least one optical density-controlling component for including in the chemical indicator; wherein the optical density-controlling component is selected from the group consisting of at least one acid; at least one polymer comprising acid groups, the polymer having an acid number of at least 7; at least one binder compound which can produce an acid when exposed to water vapor at an elevated temperature; a paper having a pH not more than 6 or a paper having a pH greater than 6; and a combination thereof;
 preparing a composition comprising:
 a) a bismuth (III) compound;
 b) elemental sulfur;
 c) a compound which makes the composition alkaline when exposed to water vapor at an elevated temperature;
 d) a binder; and, if selected,
 e) the at least one acid, the at least one polymer comprising acid groups, the at least one binder compound, or a combination thereof;
 wherein, if selected, the at least one polymer, the at least one binder compound, or a combination thereof comprises at least a portion of the binder; and
 coating the composition on at least a portion of a major surface of a substrate; wherein, if selected, the paper having a pH not more than 6 or the paper having a pH greater than 6 is the substrate.

In another embodiment, there is provided a method of determining effectiveness of a steam sterilization process, the method comprising determining whether or not sufficient removal of non-condensable gas from a steam sterilizer has occurred by:

providing a chemical indicator according to any one of chemical indicator embodiments described above and further herein below; wherein the chemical indicator is positioned within a test pack; and wherein the chemical indicator composition of the chemical indicator is located at least in an area including the center of the test pack, at least in an area at or near the edges of the test pack, and at least in an area between the edges and center of the test pack;

positioning the test pack within the steam sterilizer;

exposing the test pack to the steam sterilization process; and examining the chemical indicator composition to determine the presence or absence of a first region distinctly lighter than a second surrounding region, the first region comprising a central zone and a peripheral zone surrounding the central zone and adjacent the second surrounding region; wherein both the central zone and the peripheral zone are distinctly lighter than the second surrounding region;

wherein the presence of the first region distinctly lighter than the second surrounding region is indicative of insufficient removal of non-condensable gas, and the absence of the first region distinctly lighter than the second surrounding region is indicative of sufficient removal of non-condensable gas.

DEFINITIONS

The term "Class 1 indicator" or "Class 1 chemical indicator" refers to a chemical indicator for steam, which when tested using a resistometer undergoes a visible change as specified by ISO/FDIS 11140-1 (2005).

The term "Class 4 indicator" or "Class 4 chemical indicator" as used herein refers to a chemical indicator for steam, which when tested using a resistometer undergoes a visible change as specified by the manufacturer on exposure to steam at its stated value (for example, 134° C. for 3.5 minutes) and does not undergo a visible change or undergoes a change which is markedly different as specified by the manufacturer on exposure to steam at the stated value minus 25 percent of the stated value time and minus 2 degrees from the stated value temperature.

The term "comprising" and variations thereof (e.g., comprises, includes, etc.) do not have a limiting meaning where these terms appear in the description and claims.

As used herein, "a," "an," "the," "at least one," and "one or more" are used interchangeably, unless the context clearly dictates otherwise.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Also herein, the recitations of numerical ranges by endpoints include all numbers subsumed within that range (e.g., a weight ratio of not more than 2:3 and not less than 0.5:3 includes a weight ratio of 2:3, 1.9:3, 1.75:3, 1:3, 0.61:3, 0.5:3, etc.).

The above summary of the present invention is not intended to describe each disclosed embodiment or every implementation of the present invention. The description that follows more particularly exemplifies illustrative embodiments.

BRIEF DESCRIPTIONS OF THE DRAWINGS

FIG. 1 is plots of optical density versus time for compositions described herein.

FIG. 2 is plots of optical density versus time for compositions described herein containing a binder with acid groups and a binder which produces an acid, compared with a neutral binder after exposure to steam at 132° C. for 2.5 minutes and 134° C. for 3.5 minutes.

Figure 5:
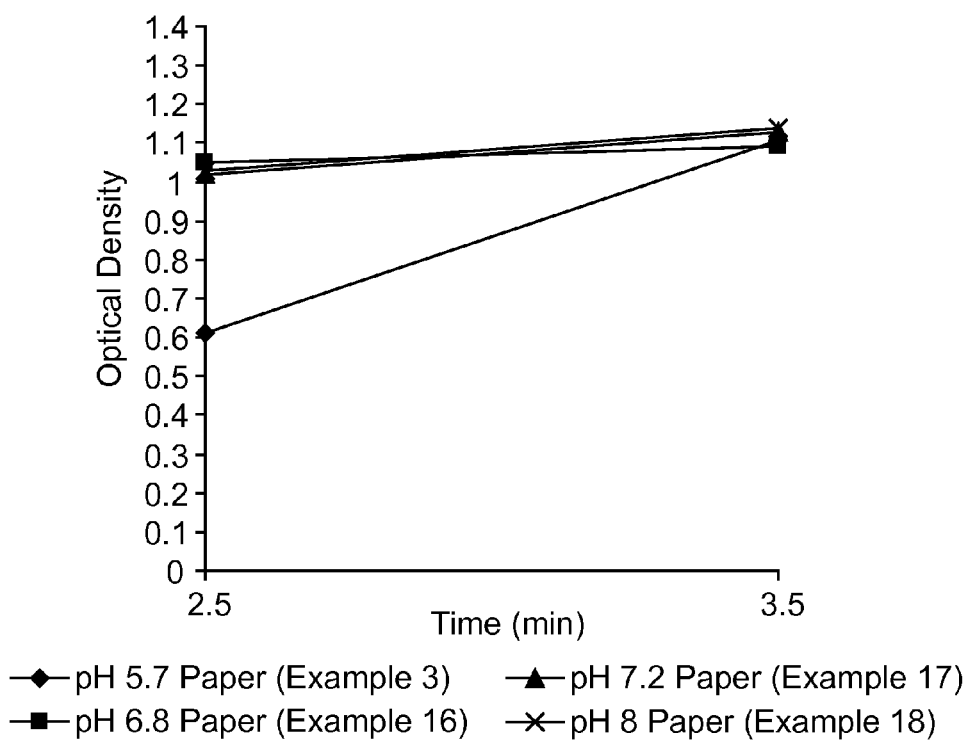

FIG. 5 is plots of optical density versus time for a composition described herein coated on paper substrates having a pH below and above 6 and after exposure to steam at 132° C. for 2.5 minutes and 134° C. for 3.5 minutes.

Figure 6:
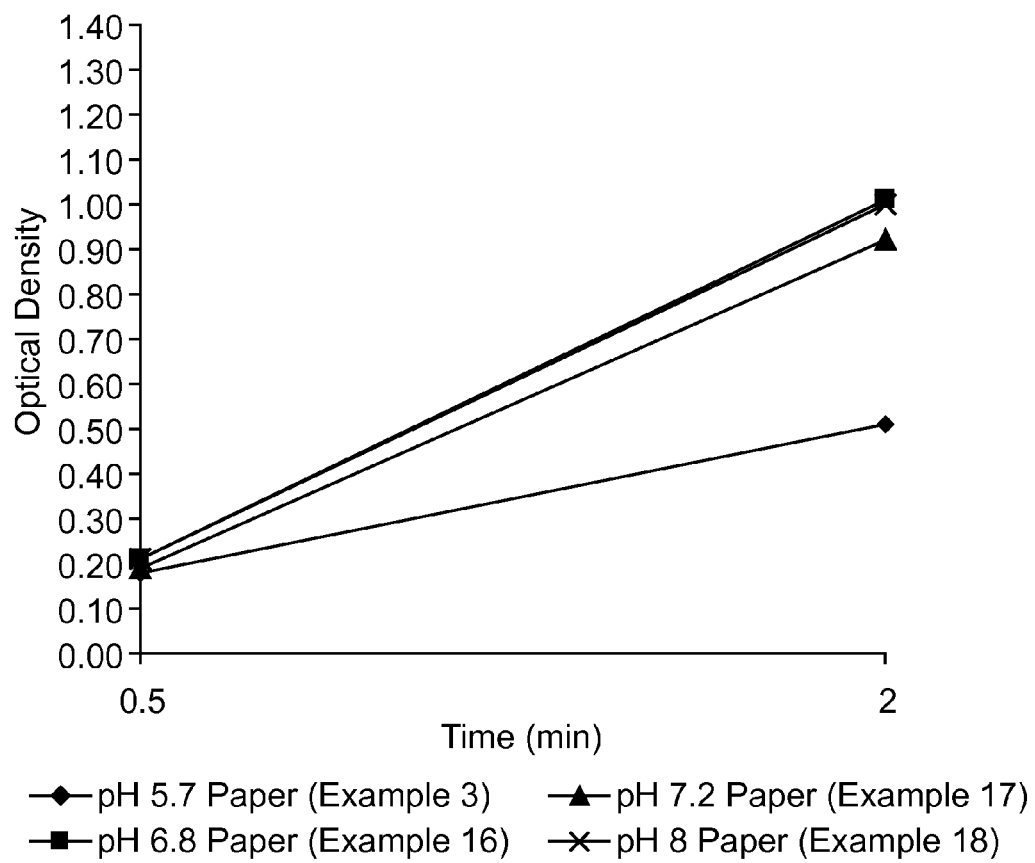

FIG. 6 is plots of optical density versus time for a composition described herein coated on paper substrates having a pH below and above 6 and after exposure to steam at 134° C. for 0.5 and 2.0 minutes.

Figure 7:
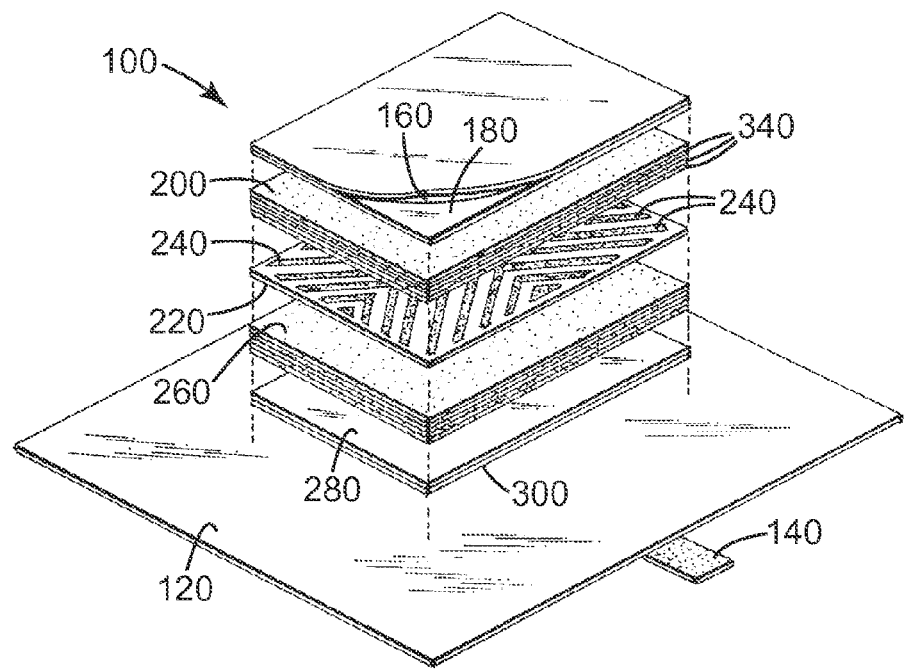

FIG. 7 is an exploded perspective view of the contents of a test pack including a chemical indicator described herein.

Figure 8:
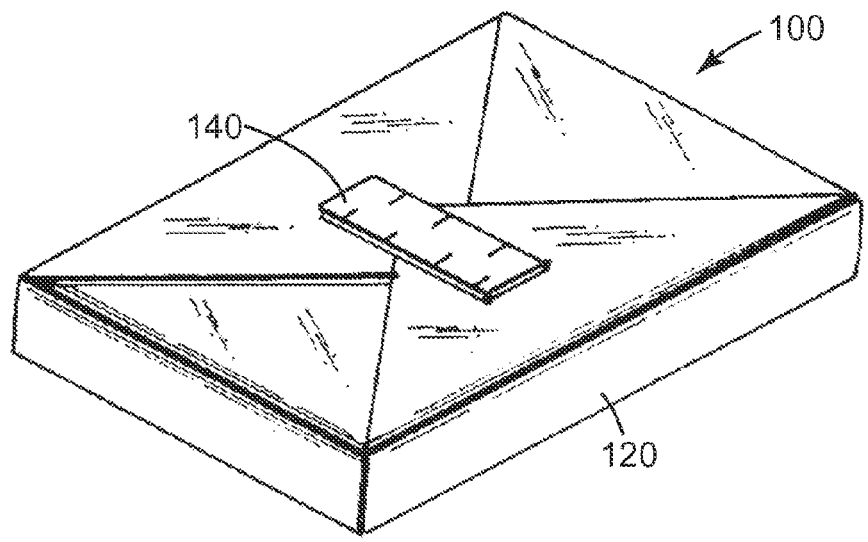

FIG. 8 is a perspective view of a test pack for positioning in a steam sterilizer.

Figure 9:
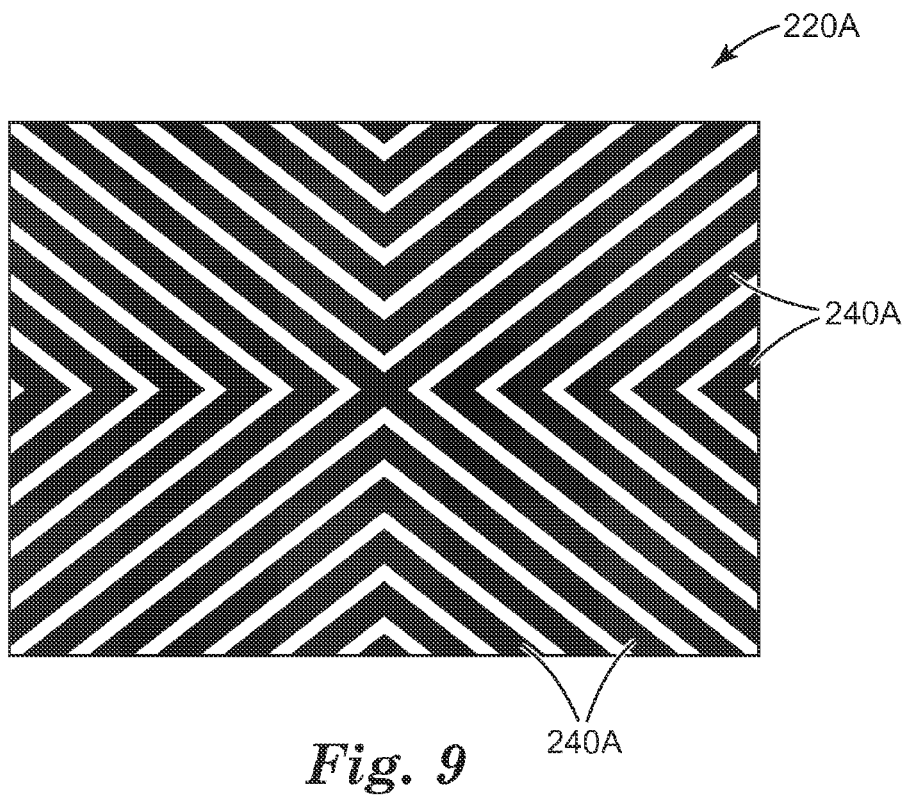

FIG. 9 is a top view of a chemical indicator described herein in the form of a Bowie-Dick indicator, also shown in FIG. 7, but darkened after exposure to a steam sterilization process.

Figure 10:
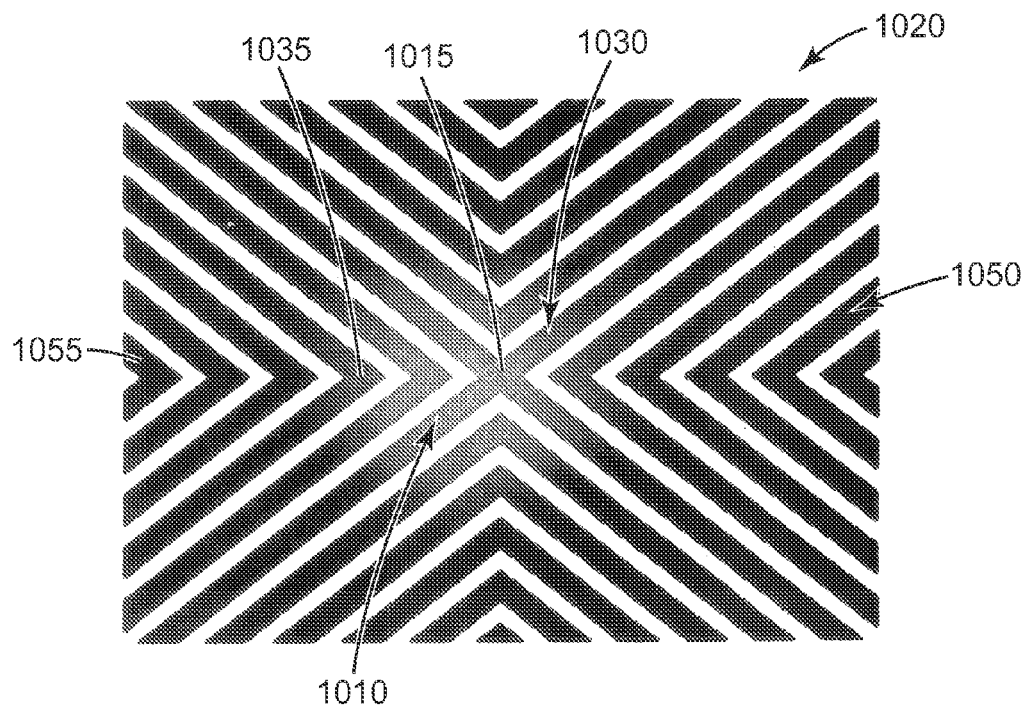

FIG. 10 is a top view of a chemical indicator described herein in the form of a Bowie-Dick indicator after exposure to a steam sterilization process with insufficient removal of non-condensable gas.

Figure 10A:
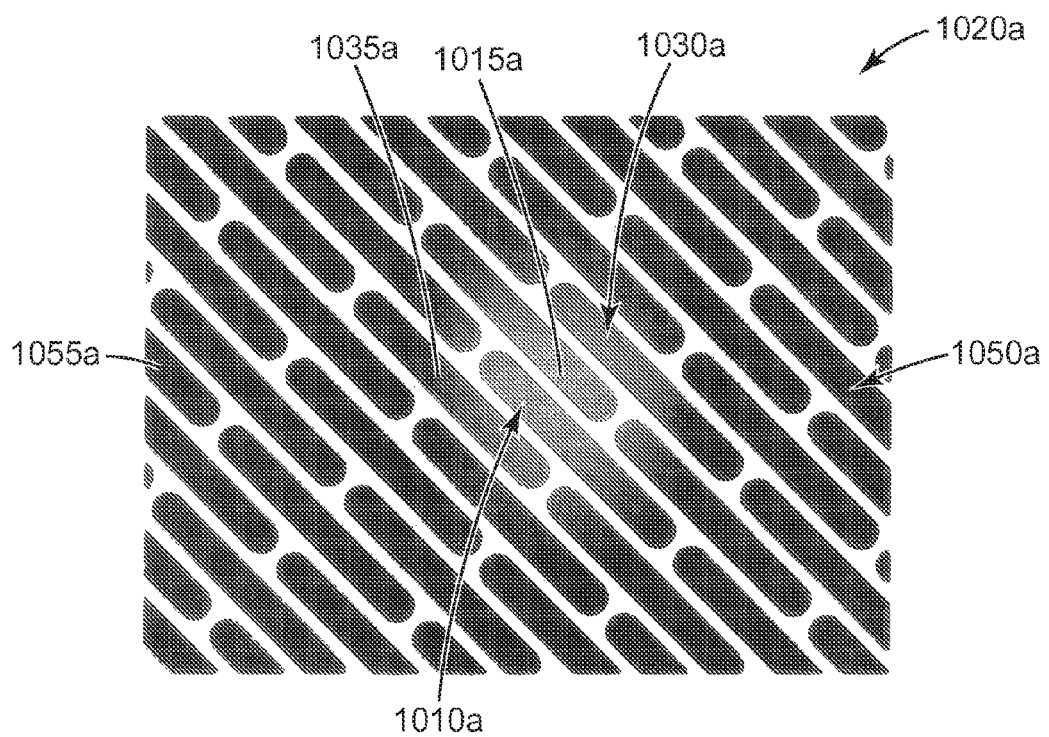

FIG. 10a is a top view of a chemical indicator described herein in the form of a Bowie-Dick indicator after exposure to a steam sterilization process with insufficient removal of non-condensable gas.

Figure 11:
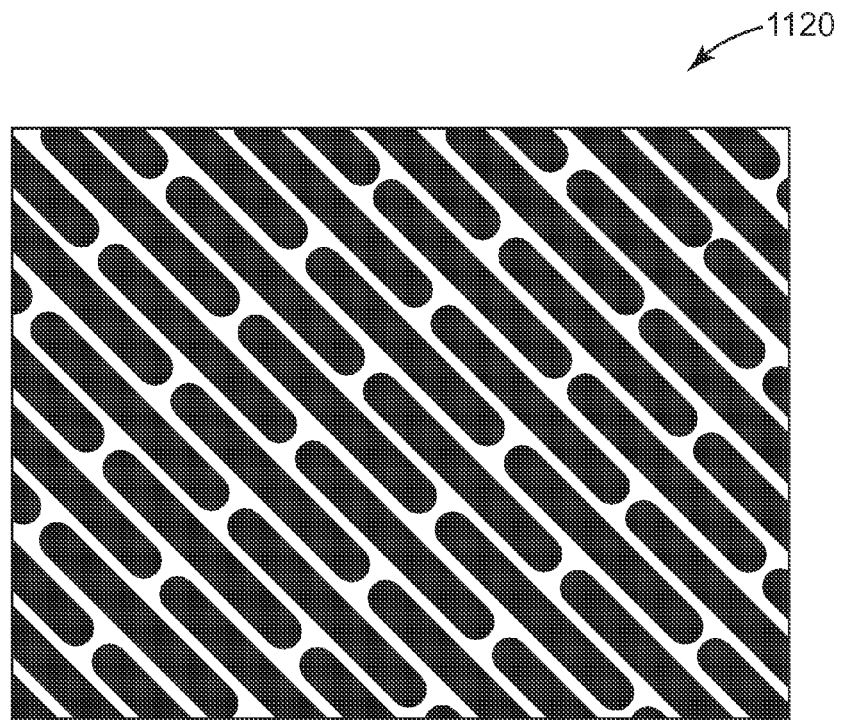

FIG. 11 is a top view of a chemical indicator described herein in the form of a Bowie-Dick indicator after exposure to a steam sterilization process.

Figure 12:
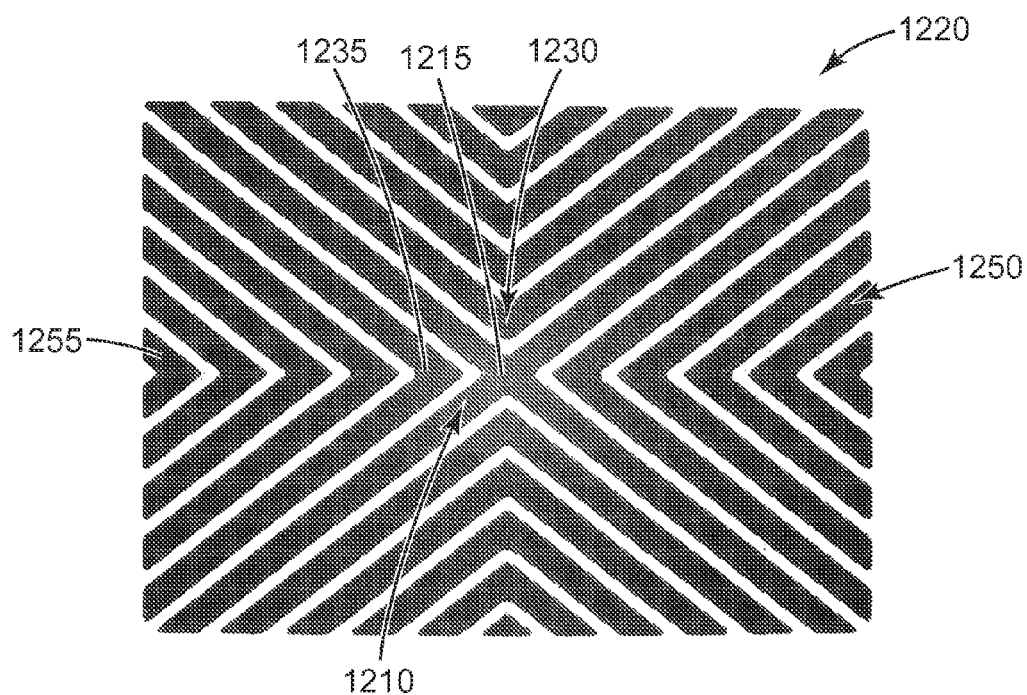

FIG. 12 is a top view of a lead carbonate-based Bowie-Dick indicator, after exposure to a steam sterilization process with insufficient removal of non-condensable gas.

Figure 13:
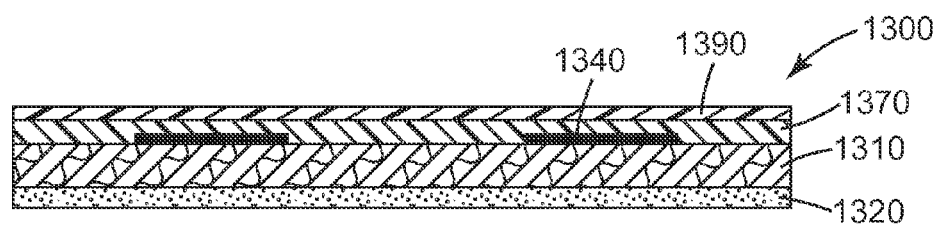

FIG. 13 is a cross-sectional view of a chemical indicator described herein in a tape form.

Figure 14:
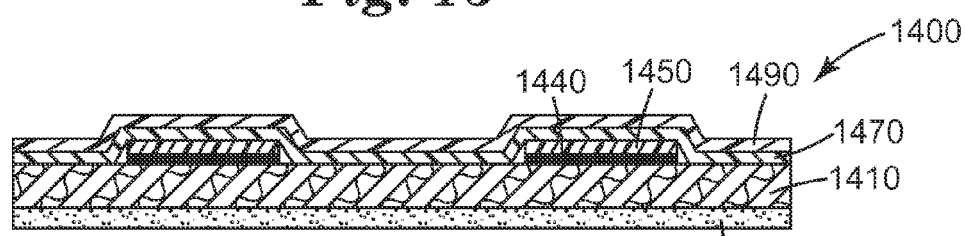

FIG. 14 is a cross-sectional view of a chemical indicator described herein in a tape form.

Figure 15:
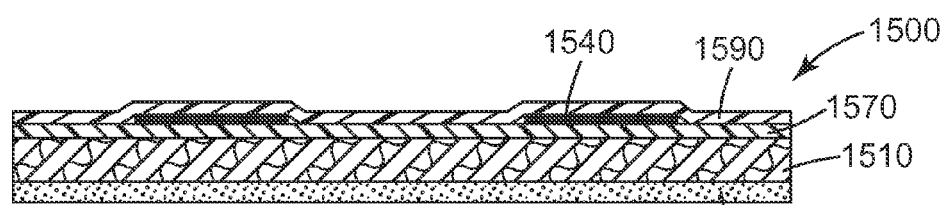

FIG. 15 is a cross-sectional view of a chemical indicator described herein in a tape form.

DETAILED DESCRIPTION OF ILLUSTRATIVE EMBODIMENTS OF THE INVENTION

Figure 1:
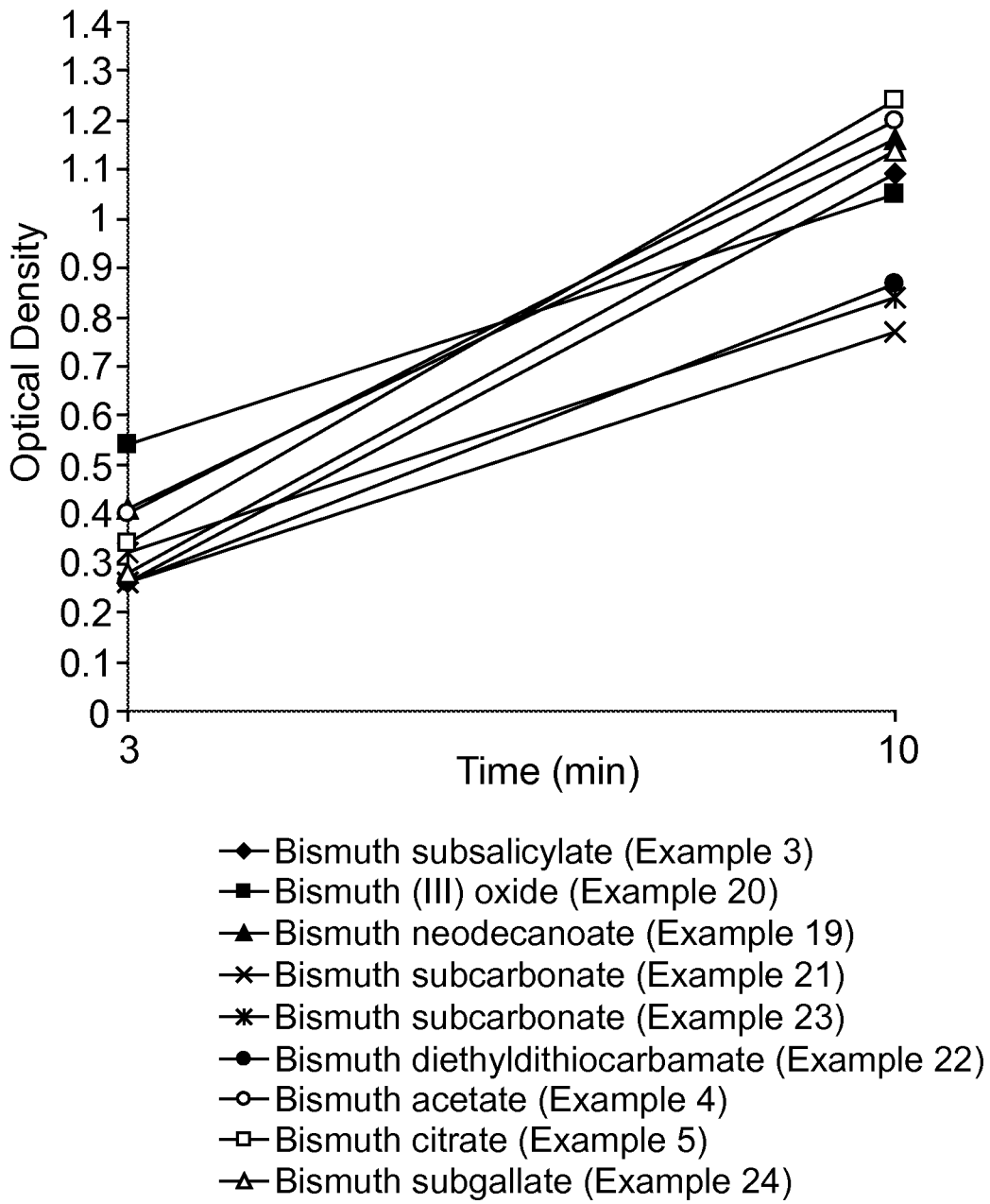

Chemical indicator compositions comprising certain bismuth compounds have now been found which become unexpectedly darker after exposure to certain steam sterilization process conditions compared with compositions comprising bismuth subcarbonate. One illustration of this is shown in FIG. 1. In one embodiment, the chemical indicator compositions comprise a bismuth (III) compound selected from the group consisting of bismuth (III) oxide and a bismuth (III) compound comprising at least one organic group which includes 2 to 20 carbon atoms; elemental sulfur; and a compound which makes the composition alkaline when exposed to water vapor at an elevated temperature.

In another embodiment, there is provided a chemical indicator comprising a substrate and a chemical indicator composition coated on at least a portion of a major surface of the substrate, the composition comprising a bismuth (III) compound selected from the group consisting of bismuth (III) oxide and a bismuth (III) compound comprising at least one organic group which includes 2 to 20 carbon atoms; elemental sulfur; and a compound which makes the composition alkaline when exposed to water vapor at an elevated temperature.

In another embodiment, there is provided a chemical indicator composition comprising a bismuth compound; elemental sulfur; a compound which makes the composition alkaline when exposed to water vapor at an elevated temperature; and at least one acid other than any acid present in the bismuth compound.

In another embodiment, there is provided a chemical indicator comprising a substrate and a chemical indicator composition comprising a bismuth compound; elemental sulfur; a compound which makes the composition alkaline when exposed to water vapor at an elevated temperature; and at least one acid other than any acid present in the bismuth compound.

For certain embodiments, including the above embodiments where the composition includes at least one acid other than any acid present in the bismuth compound, the bismuth compound is an inorganic bismuth compound, an organic bismuth compound, or a combination thereof. For certain of these embodiments, the inorganic bismuth compound is selected from the group consisting of bismuth (III) oxide, bismuth subcarbonate, bismuth borate, bismuth titanate, bismuth molybdate, bismuth phosphate, and bismuth oxychloride. For certain of these embodiments, the organic bismuth compound is a bismuth (III) compound comprising at least one organic group which includes 2 to 20 carbon atoms. For certain of these embodiments, the bismuth compound is the inorganic bismuth compound. For certain of these embodiments, the inorganic bismuth compound is bismuth (III) oxide. Alternatively, for certain of these embodiments, the bismuth compound is the organic bismuth compound. Alternatively, for certain of these embodiments, the bismuth compound is a combination of the organic bismuth compound and the inorganic bismuth compound.

For certain embodiments, including any one of the above composition and indicator embodiments, the bismuth (III) compound is a bismuth (III) compound comprising at least one organic group which includes 2 to 20 carbon atoms. For certain of these embodiments, the bismuth (III) compound is selected from the group consisting of bismuth subsalicylate (CAS Reg. No. 14882-18-9), bismuth gallate (3,4,5-trihydroxybenzoic acid bismuth salt, CAS Reg. No. 57206-57-2), bismuth subgallate (2,7-dihydroxy-1,3,2-benzodioxabismol-5-carboxylic acid, CAS Reg. No. 99-26-3), bismuth pyrogallate (1,2,3-benzenetriol, bismuth salt, basic, CAS Reg. No. 12001-49-9), bismuth acetate (bismuth triacetate, CAS Reg. No. 22306-37-2), bismuth citrate (CAS Reg. No. 110230-89-2), bismuth potassium citrate (CAS Reg. No. 57644-54-9), ammonium bismuth citrate (CAS Reg. No. 67953-07-5), bismuth lactate (CAS Reg. No. 6591-53-3), bismuth oxalate (CAS Reg. No. 6591-55-5), bismuth benzoate, bismuth formate, bismuth propionate, bismuth butyrate, bismuth pivalate (bismuth salt of 2,2-dimethylpropanoic acid), 2-propylpentanoic acid bismuth salt (CAS Reg. No. 94071-09-7), bismuth ascorbate, bismuth diethyldithiocarbamate (tris(diethyldithiocarbamato) bismuth (III), CAS Reg. No. 20673-31-8), bismuth dimethyldithiocarbamate, bismuth 2-ethylhexanoate (CAS Reg. No. 67874-71-9), bismuth neodecanoate (CAS Reg. No. 34364-26-6), bismuth oleate, bismuth gluconate, bismuth potassium D-gluconate, bismuth naphtholate (CAS Reg. No. 8039-60-9), naphthenic acid bismuth salt (CAS Reg. No. 85736-59-0), bismuth triglycollamate, bismuth sodium triglycollamate (N,N-bis(carboxymethyl)glycine disodium salt/N-(carboxymethyl)-N-[2-oxo-2-{(oxobismuthino)oxy}ethyl]glycine monosodium salt (3:1), CAS Reg. No. 5798-43-6), bismuth succinate (CAS Reg. No. 139-16-2), bismuth maleate (CAS Reg. No. 88210-84-8), bismuth tartrate (CAS Reg. No. 6591-56-6), bismuth sodium tartrate (CAS Reg. No. 31586-77-3), bismuth potassium tartrate (CAS Reg. No. 5798-41-4), bismuth tannate, 3-camphocarboxylic acid bismuth salt (CAS Reg. No. 4154-53-4), bismuth ethylcamphorate (CAS Reg. No. 52951-37-8), bismuth oxyquinoline (CAS Reg. No. 1300-75-0), 2-oxo-3-bornanecarboxylic acid bismuth salt (CAS Reg. No. 19495-28-4), bismuth valproate, and a combination thereof. Any of the compounds having at least one chiral center includes any one of the stereoisomers or any combination thereof, including racemic mixtures. For example, bismuth gluconate includes all forms of the gluconate (e.g., D-gluconic acid bismuth (III) salt (CAS Reg. No. 94232-39-0), L-gluconic acid bismuth (III) salt, and/or a racemic mixture thereof. For certain of these embodiments, the bismuth (III) compound is selected from the group consisting of bismuth subsalicylate, bismuth subgallate, bismuth acetate, bismuth citrate, bismuth neodecanoate, and a combination thereof. For certain of these embodiments, the bismuth (III) compound is bismuth subsalicylate.

For certain embodiments, including any one of the above composition and indicator embodiments, except where the bismuth (III) compound is a bismuth (III) compound comprising at least one organic group which includes 2 to 20 carbon atoms, the bismuth (III) compound is bismuth (III) oxide.

Elemental sulfur is known to exist as an eight membered ring of sulfur atoms. Under certain alkaline conditions, for example, in the presence of a nucleophile, such as hydroxide ion, the ring of sulfur atoms can be opened, and sulfide ions can be formed from the resulting chain of sulfur atoms. In the presence of the sulfide ions, the bismuth compound can form bismuth sulfide which is a dark color.

The compound which makes the composition alkaline when exposed to water vapor at an elevated temperature is believed to bring about conditions whereby sulfide ions are formed. Compounds suitable for this purpose include, for example, sodium carbonate, sodium bicarbonate, barium hydroxide, lithium carbonate, magnesium carbonate, calcium carbonate, barium carbonate, calcium hydroxide, magnesium hydroxide, as well as salts of organic acids having a relatively low pKa, for example, sodium acetate, and potassium and lithium salts of 2,4-dihydroxybenzoic acid and 2,4,6-trihydroxybenzoic acid. Compounds which have a relatively high solubility in water have been found to cause the compositions and indicators to darken prematurely or earlier than desired during exposure to steam sterilization process conditions. In addition, this can cause the optical density of the composition after exposure to a steam sterilization process condition known to be insufficient for bringing about sterilization to be undesirably similar to the optical density of the composition after exposure to a sterilization effective condition. Accordingly, for certain embodiments, including any one of the composition, indicator, and method embodiments described herein, preferably the compound which makes the composition alkaline has a solubility in water at 100° C. of not more than 1 gram per 100 cubic centimeters of water. For certain of these embodiments, the compound which makes the composition alkaline is selected from the group consisting of lithium carbonate, magnesium carbonate, calcium carbonate, barium carbonate, calcium hydroxide, magnesium hydroxide, or a combination thereof. For certain of these embodiments, the compound which makes the composition alkaline is lithium carbonate.

For certain embodiments, including any one of the above composition and indicator embodiments, the composition further comprises a binder. The binder holds the composition in place when coated on a substrate. Preferably the binder comprises a film-forming material, which is stable to heat and water vapor. A film formed by the binder is sufficiently permeable to water vapor and steam to allow a desired color change to occur under sterilization conditions. Materials which the binder may comprise include, for example, acrylate and methacrylate polymers and copolymers (e.g., poly(methylmethacrylate) and methyl/n-butyl methacrylate copolymer), poly(vinyl acetate) and poly(vinylchloride) and copolymers thereof, and various derivatives of cellulose, including, for example, ethylcellulose and nitrocellulose. In certain embodiments, the binder may be an ultraviolet light, visible light, or thermally curable material. Preferably, such materials are used without solvent.

It has now been found that compositions comprising a sufficiently acidic binder can provide a significant increase in the difference between the optical density after exposure to steam at 132° C. for 2.5 minutes and 134° C. for 3.5 minutes. A Class 4 chemical indicator wherein indications of pass and fail can be more readily and reliably distinguished can, therefore, be provided. Accordingly, for certain embodiments, including any one of the above composition and indicator embodiments, the binder comprises a polymer comprising acid groups, wherein the binder has an acid number of at least 7. For certain of these embodiments, the binder comprises an acrylate polymer, a methacrylate polymer, an acrylate copolymer, a methacrylate copolymer, an acrylate/methacrylate copolymer, or a combination thereof, wherein the polymer or copolymer comprises sufficient carboxylic acid groups for an acid number of at least 7. For certain of these embodiments, preferably the acid number is at least 8 or at least 9. For certain of these embodiments, the binder comprises a methyl/n-butyl methacrylate copolymer.

Binders which are sufficiently acidic by producing an acid when exposed to water vapor at an elevated temperature may also be used, although a polymer comprising acid groups is preferred. In one example, nitrocellulose can form nitric acid when exposed to steam. Accordingly, for certain embodiments, including any one of the above composition and indicator embodiments, the binder comprises a compound which can produce an acid when exposed to water vapor at an elevated temperature. For certain of these embodiments, the compound which can produce the acid is present in an amount which can produce at least 0.005 equivalents acid per equivalent of the compound which makes the composition alkaline.

It has also now been found that compositions comprising an acid can provide a significant increase in the difference between the optical density after exposure to steam at 134° C. for 0.5 minutes and 134° C. for 2.0 minutes, and/or a significant increase in optical density after exposure to the steam at 134° C. for 2.0 minutes, at 121° C. for 10 minutes, or at 134° C. for 3.5 minutes. A Class 1 or Class 4 chemical indicator wherein indications of pass and fail can be more readily and reliably distinguished can, therefore, be provided. Accordingly, for certain embodiments, including any one of the above composition and indicator embodiments, except those which already include an acid, the composition further comprises at least one acid. The at least one acid is other than any acid functionality present in the bismuth compound.

For certain embodiments, including any one of the above embodiments which includes the at least one acid, the acid is a solid at a temperature of at least 100° C. This may provide for a more stable composition when the composition exists as a coating on a substrate. Such solid acids may be less likely to leach out of the coating than acids which are liquids during manufacturing and storage or during exposure to a sterilization process condition.

For certain embodiments, including any one of the above embodiments which includes the at least one acid, the acid is present in an amount of at least 0.005 equivalents acid per equivalent of the compound which makes the composition alkaline. For certain of these embodiments, the acid is present in an amount of at least 0.025 or 0.05 equivalents acid per equivalent of the compound which makes the composition alkaline. For certain of these embodiments, the acid is present in an amount wherein less than one equivalent acid is present per equivalent of the compound which makes the composition alkaline.

For certain embodiments, including any one of the above embodiments which includes the at least one acid, the acid is selected from the group consisting of 2-hydroxybenzoic acid, benzoic acid, p-toluenesulfonic acid, phenylacetic acid, citric acid, phthalic acid, suberic acid, and a combination thereof. For certain of these embodiments, the acid is selected from the group consisting of 2-hydroxybenzoic acid, benzoic acid, p-toluenesulfonic acid, phenylacetic acid, suberic acid, and a combination thereof.

Compositions and indicators described herein provide good optical density differentiation between fail and pass steam sterilization conditions. For example, the optical density of a composition exposed to steam at 134° C. for 0.5 minutes or steam at 121° C. for 3 minutes (which are considered to be fail steam sterilization conditions for a Class 1 indicator) can be clearly seen to be lower than when the composition is exposed to steam at 134° C. for 2.0 minutes or steam at 121° C. for 10 minutes (which may be considered to be pass steam sterilization conditions for a Class 1 indicator). For certain embodiments, including any one of the above composition and indicator embodiments, when exposed to a first condition selected from the group consisting of steam at a temperature of 134° C. for 2 minutes and steam at a temperature of 121° C. for 10 minutes, the composition undergoes a change in optical density resulting in an optical density of at least 0.4, and wherein when instead exposed to a second condition selected from the group consisting of steam at a temperature of 134° C. for 0.5 minutes and steam at a temperature of 121° C. for 3 minutes, any change in optical density is at least 0.3 optical density units less than when exposed to the first condition. For certain of these embodiments, when exposed to the first condition, the composition undergoes a change in optical density resulting in an optical density of at least 0.5.

It has now been further found that the indicators described herein comprising a paper substrate having a pH not greater than 6 can provide a significant increase in the difference between the optical density after exposure to steam at 132° C. for 2.5 minutes and 134° C. for 3.5 minutes. A Class 4 chemical indicator wherein indications of pass and fail can be more readily and reliably distinguished can, therefore, be provided.

Accordingly, for certain embodiments, including any one of the above indicator embodiments, the substrate is a paper with a pH of not more than 6. For certain of these embodiments, wherein when exposed to steam at a temperature of 134° C. for 3.5 minutes, the composition undergoes a change in optical density resulting in an optical density of at least 0.8, and wherein when instead exposed to steam at a temperature of 132° C. for 2.5 minutes, any change in optical density is at least 0.4 optical density units less than when exposed to steam at the temperature of 134° C. for 3.5 minutes.

Indicators described herein comprising a paper substrate having a pH not greater than 6 may also provide an increase in the difference between the optical density after exposure to steam at 121° C. for 3.0 minutes and 121° C. for 10 minutes. Accordingly, for certain embodiments where the substrate is a paper with a pH of not more than 6, when exposed to steam at a temperature of 121° C. for 10 minutes, the composition undergoes a change in optical density resulting in an optical density of at least 0.8, and wherein when instead exposed to steam at a temperature of 121° C. for 3 minutes, any change in optical density is at least 0.7 optical density units less than when exposed to steam at the temperature of 121° C. for 10 minutes.

It has now also been found that the indicators described herein comprising a paper substrate having a pH greater than 6 can provide a significant increase in the difference between the optical density after exposure to steam at 134° C. for 0.5 minutes and 134° C. for 2.0 minutes. A Class 1 chemical indicator wherein indications of pass and fail can be more readily and reliably distinguished can, therefore, be provided. Accordingly, for certain embodiments, including any one of the above indicator embodiments, except those with a paper substrate with a pH not more than 6, the substrate is a paper with a pH greater than 6. For certain of these embodiments, when exposed to steam at a temperature of 134° C. for 2.0 minutes, the composition undergoes a change in optical density resulting in an optical density of at least 0.8, and wherein when instead exposed to steam at a temperature of 134° C. for 0.5 minutes, any change in optical density is at least 0.4 optical density units less than when exposed to steam at the temperature of 134° C. for 2.0 minutes. For certain of these embodiments, any change in optical density is at least 0.6 optical density units less than when exposed to steam at the temperature of 134° C. for 2.0 minutes. For certain of these embodiments, the pH is greater than 6.5.

Not only can compositions and indicators described herein provide good optical density differentiation between fail and pass steam sterilization conditions, but a darker color can be achieved when exposed to a pass steam sterilization condition. For certain embodiments, including any one of the above composition and indicator embodiments, when exposed to a first condition selected from the group consisting of steam at a temperature of 134° C. for 2 minutes and steam at a temperature of 121° C. for 10 minutes, the composition changes color to brown or black. For certain of these embodiments, when exposed to the first condition the composition undergoes a change in optical density resulting in an optical density of at least 1.0, and wherein the first condition is steam at a temperature of 121° C. for 10 minutes. A Class 1 chemical indicator wherein indications of pass and fail can be more readily and reliably distinguished can, thereby, be provided.

For certain embodiments, including any one of the above composition and indicator embodiments, when exposed to steam at 134° C. for 3.5 minutes the composition undergoes a change in optical density resulting in an optical density of at least 1.0, and wherein when instead exposed to steam at a temperature of 132° C. for 2.5 minutes, any change in optical density is at least 0.3 optical density units less than when exposed steam at 134° C. for 3.5 minutes. A Class 4 chemical indicator wherein indications of pass and fail can be more readily and reliably distinguished can, thereby, be provided.

Relatively low ratios of bismuth to the other components in the compositions have now been found to be effective in providing the desired properties described herein. As a result, the amounts of bismuth used in the compositions and indicators described herein can be reduced relative to previously known chemical indicator compositions. For certain embodiments, including any one of the above composition and indicator embodiments, the bismuth (III) compound and the elemental sulfur are present in the composition in a weight ratio of not more than 2:3 and not less than 0.5:3; and wherein the elemental sulfur and the compound which makes the composition alkaline are present in a weight ratio of not more than 1:1 and not less than 1:5.

As indicated above, the present invention also provides a method of determining the effectiveness of a steam sterilization process, the method comprising providing a chemical indicator according to any one of the indicator embodiments described above; placing the chemical indicator in a steam sterilization chamber; exposing the chemical indicator to steam at a temperature of at least 121° C.; and determining an optical density of the chemical indicator. The indicators described herein produce a significantly increased optical density when exposed to a steam sterilization process condition classified as a pass condition. When exposed to a steam sterilization process condition classified as a fail condition, any increase in optical density produced by the indicator is readily discerned from that produced by the pass condition.

For certain embodiment of the above method, the method further comprises placing an article to be sterilized along with the sterilization process indicator in the sterilization chamber. The article is then exposed to the same sterilization conditions as the chemical indicator.

For certain embodiments, including any one of the above method embodiments, the method further comprises determining whether or not sterilization conditions were met in the sterilization chamber. For example, upon exposure to sterilization conditions targeted for 121° C. for 10 minutes, these sterilization conditions are determined to have been met when the chemical indicator produces an optical density in a range known to indicate exposure to these conditions. On the other hand, when exposed to inadequate sterilization conditions the chemical indicator produces an optical density below an optical density range known to be produced by the indicator at 121° C. for 10 minutes, and sterilization conditions are determined not to have been met. The characteristics of the compositions and indicators described above make determining whether or not sterilization conditions were met in the sterilization chamber easier and more reliable.

As indicated above, the present invention also provides a method of making a chemical indicator having a targeted change in optical density when exposed to a steam sterilization process condition; the method comprising: selecting at least one optical density-controlling component for including in the chemical indicator; wherein the optical density-controlling component is selected from the group consisting of at least one acid; at least one polymer comprising acid groups, the polymer having an acid number of at least 7; at least one binder compound which can produce an acid when exposed to water vapor at an elevated temperature; a paper having a pH not more than 6, a paper having a pH greater than 6; and a combination thereof; preparing a composition comprising: a) a bismuth (III) compound; b) elemental sulfur; c) a compound which makes the composition alkaline when exposed to water vapor at an elevated temperature; d) a binder; and, if selected, e) the at least one acid, the at least one polymer comprising acid groups, the at least one binder compound, or a combination thereof; wherein, if selected, the at least one polymer, the at least one binder compound, or a combination thereof comprises at least a portion of the binder; and coating the composition on at least a portion of a major surface of a substrate; wherein, if selected, the paper having a pH not more than 6, the paper having a pH greater than 6, or both are the substrate. For certain of these embodiments, preferably the optical density-controlling component is selected from the group consisting of at least one acid; at least one polymer comprising acid groups, the polymer having an acid number of at least 7; a paper having a pH not more than 6; a paper having a pH greater than 6; and a combination thereof. For certain of these embodiments, the optical density-controlling component is selected from the group consisting of at least one acid; a paper having a pH greater than 6; and a combination thereof. For certain of these embodiments, the targeted change in optical density when exposed to a steam sterilization process condition is for a Class 1 chemical indicator. Alternatively, for certain of these embodiments, the optical density-controlling component is selected from the group consisting of at least one acid; at least one polymer comprising acid groups, the polymer having an acid number of at least 7; a paper having a pH not more than 6; and a combination thereof. For certain of these embodiments, the targeted change in optical density when exposed to a steam sterilization process condition is for a Class 4 chemical indicator.

For certain embodiments, including any one of the above embodiments of the method of making a chemical indicator the at least one polymer comprising acid groups is selected. For certain of these embodiments, wherein when exposed to steam at a temperature of 134° C. for 3.5 minutes, the composition (wherein the binder comprises the at least one polymer comprising acid groups) undergoes a change in optical density resulting in an optical density of at least 0.8, and wherein when instead exposed to steam at a temperature of 132° C. for 2.5 minutes, any change in optical density is at least 0.3 optical density units less than when exposed to steam at the temperature of 134° C. for 3.5 minutes. A Class 4 chemical indicator wherein indications of pass and fail can be more readily and reliably distinguished can, thereby, be provided.

For certain embodiments, including any one of the above embodiments of the method of making a chemical indicator, the at least one acid is selected. For certain of these embodiments, wherein when exposed to steam at a temperature of 134° C. for 2.0 minutes, the composition undergoes a change in optical density resulting in an optical density of at least 0.6, and wherein when instead exposed to steam at a temperature of 134° C. for 0.5 minutes, any change in optical density is at least 0.5 optical density units less than when exposed to steam at the temperature of 134° C. for 2.0 minutes. The at least one acid can be any one of the embodiments thereof described above. A Class 1 chemical indicator wherein indications of pass and fail can be more readily and reliably distinguished can, thereby, be provided.

For certain embodiments, including any one of the above embodiments of the method of making a chemical indicator, the paper having a pH not more than 6 is selected. For certain of these embodiments, when exposed to steam at a temperature of 134° C. for 3.5 minutes, the composition undergoes a change in optical density resulting in an optical density of at least 1.0, and wherein when instead exposed to steam at a temperature of 132° C. for 2.5 minutes, any change in optical density is at least 0.4 optical density units less than when exposed to steam at the temperature of 134° C. for 3.5 minutes. A Class 4 chemical indicator wherein indications of pass and fail can be more readily and reliably distinguished can, thereby, be provided. For certain embodiments, when exposed to steam at a temperature of 121° C. for 10 minutes, the composition undergoes a change in optical density resulting in an optical density of at least 1.0, and wherein when instead exposed to steam at a temperature of 121° C. for 3.0 minutes, any change in optical density is at least 0.7 optical density units less than when exposed to steam at the temperature of 121° C. for 10 minutes. A Class 1 chemical indicator, wherein indications of pass and fail when exposed to steam at 121° C. can be more readily and reliably distinguished, can, thereby, be provided.

For certain embodiments, including any one of the above embodiments of the method of making a chemical indicator, the paper having a pH greater than 6 is selected. When the paper having a pH not more than 6 is also selected, the indicator includes two or more indicators within the same indicator (e.g., at least one indicator with paper having a pH not more than 6 as its substrate and at least one indicator with paper having a pH greater than 6 as its substrate). Otherwise, selection of the paper having a pH greater than 6 does not apply to the above embodiments wherein the paper having a pH not more than 6 is selected. For certain of these embodiments, for the indicator with paper having a pH greater than 6 when exposed to steam at a temperature of 134° C. for 2.0 minutes, the composition undergoes a change in optical density resulting in an optical density of at least 0.8, and wherein when instead exposed to steam at a temperature of 134° C. for 0.5 minutes, any change in optical density is at least 0.4 optical density units less than when exposed to steam at the temperature of 134° C. for 2.0 minutes. A Class 1 chemical indicator wherein indications of pass and fail can be more readily and reliably distinguished can, thereby, be provided. For certain of these embodiments, preferably any change in optical density is at least 0.6 optical density units less than when exposed to steam at the temperature of 134° C. for 2.0 minutes.

For certain embodiments, including any one of the above embodiments of the method of making a chemical indicator, the bismuth (III) compound is as described in any one of the above composition and indicator embodiments.

For certain embodiments, including any one of the above embodiments of the method of making a chemical indicator, except where the binder comprises the polymer having an acid number of at least 7, the binder has an acid number of 0 to less than 7. For certain of these embodiments, when exposed to steam at a temperature of 134° C. for 2.0 minutes, the chemical indicator composition undergoes a change in optical density resulting in an optical density of at least 0.8, and wherein when instead exposed to steam at a temperature of 134° C. for 0.5 minutes, any change in optical density is at least 0.5 optical density units less than when exposed to steam at the temperature of 134° C. for 2.0 minutes. A Class 1 chemical indicator wherein indications of pass and fail can be more readily and reliably distinguished can, thereby, be provided.

For certain embodiments, including any one of the above embodiments of the method of making a chemical indicator, the compound which makes the composition alkaline is as described in any one of the above composition and indicator embodiments.

For certain embodiments, including any one of the above embodiments of the method of making a chemical indicator, the bismuth (III) compound and the elemental sulfur are present in the composition in a weight ratio of not more than 2:3 and not less than 0.5:3; and wherein the elemental sulfur and the compound which makes the composition alkaline are present in a weight ratio of not more than 1:1 and not less than 1:5.

As indicated above, the present invention also provides a method of determining effectiveness of a steam sterilization process, the method comprising determining whether or not sufficient removal of non-condensable gas from a steam sterilizer has occurred. In one embodiment, the method comprises providing a chemical indicator according to any one of the above chemical indicator embodiments, wherein the chemical indicator is positioned within a test pack. The chemical indicator composition of the chemical indicator is located at least in an area including the center of the test pack, at least in an area at or near the edges of the test pack, and at least in an area between the edges and center of the test pack. The method further comprises positioning the test pack within the steam sterilizer, exposing the test pack to the steam sterilization process, and examining the chemical indicator composition to determine the presence or absence of a first region distinctly lighter than a second surrounding region. The first region if present comprises a central zone and a peripheral zone surrounding the central zone and adjacent the second surrounding region, wherein both the central zone and the peripheral zone are distinctly lighter than the second surrounding region. The presence of a first region distinctly lighter than the second surrounding region is indicative of insufficient removal of non-condensable gas, and the absence of a first region distinctly lighter than the second surrounding region is indicative of sufficient removal of non-condensable gas.

The presence of the first region distinctly lighter than the second surrounding region is the result of the presence of an air pocket or a volume of a non-condensable gas residing in the test pack in this region of the chemical indicator. Such a pocket, when present, may be located generally in the middle of the test pack, in which case the second surrounding region fully surrounds the first distinctly lighter region. Alternatively, depending upon the position of the test pack within the steam sterilizer, such a pocket, when present, may be located toward or at one edge of the test pack, in which case, the second surrounding region may partially surround the first distinctly lighter region. Accordingly, the term surround with respect to the second surrounding region may mean to fully surround or to partially surround the distinctly lighter region.

FIGS. 10 and 10a illustrate embodiments of the present chemical indicator in the present method, chemical indicators 1020 and 1020a, in which an air pocket was present approximately in the middle of the test pack in which chemical indicators 1020 and 1020a resided during the steam sterilization process. Second surrounding regions 1050 and 1050a of chemical indicators 1020 and 1020a are dark, indicating full contact with the steam. A first distinctly lighter region in each chemical indicator 1020 and 1020a includes central zone 1010 and 1010a, respectively and peripheral zone 1030 and 1030a, respectively. Peripheral zones 1030 and 1030a surround central zones 1010 and 1010a, respectively and are adjacent second surrounding regions 1050 and 1050a, respectively.

Both peripheral zones (1030 and 1030a) and central zones (1010 and 1010a), where only partial contact with the steam occurred as a result of the air pocket, are distinctly lighter than second surrounding regions (1050 and 1050a). This is in contrast to the comparative lead carbonate indicator 1220 shown in FIG. 12. An air pocket was also present under the same conditions as encountered by the chemical indicators 1020 and 1020a of FIGS. 10 and 10a. Although not as readily discernable, lighter region 1210 is shown in FIG. 12. However, zone 1230 immediately peripheral to lighter region 1210 blends into surround region 1250 and is not distinctly lighter than 1250. For example, the difference between optical densities in region 1250 and zone 1230 may be less than 0.10, 0.09, 0.07, or even 0.05 optical density units.

Using the chemical indicator bearing the chemical indicator compositions disclosed herein, can, therefore, in certain embodiments, provide improved and more reliable visual recognition of the presence or absence of an air pocket or volume of a non-condensable gas. For certain embodiments, examining the chemical indicator composition is carried out visually. Alternatively or additionally, examining the chemical indicator composition is carried out photometrically. For example, a device may be used to measure absorbance or reflectance of the chemical indicator composition on the chemical indicator.

For certain embodiments, including any one of the above method embodiments, optical density of the chemical indicator composition in the central zone and optical density of the chemical indicator composition in the area at or near the edges of the test pack within the second surrounding region are measured and differ from each other by at least 0.30 optical density units when removal of the non-condensable gas is not sufficient under Air Leak Test Condition I. In certain embodiments, the optical densities differ from each other by not more than 0.05 optical density units when removal of the non-condensable gas is sufficient (for example, wherein there is no air leak in the sterilizer).

For certain embodiments, including any one of the above method embodiments, alternatively or additionally, optical density of the chemical indicator composition in the peripheral zone and optical density of the chemical indicator composition in the area at or near the edges of the test pack within the second surrounding region are measured and differ from each other by at least 0.15 optical density units when removal of the non-condensable gas was not sufficient with under Air Leak Test Condition I; and the optical densities differ from each other by less than 0.05 optical density units when removal of the non-condensable gas is sufficient.

FIG. 9 illustrates a chemical indicator 220A taken from a test pack used in the above method, in which sufficient removal of non-condensable gas was accomplished and no significant air pocket, if any, was encountered by the chemical indicator. No lighter region is apparent in chemical indicator composition 240A, and optical density differences between areas is very low, e.g., less than 0.05 optical density units.

Improved and more reliable visual recognition of the presence or absence of an air pocket or volume of a non-condensable gas using the chemical indicator bearing the chemical indicator compositions disclosed herein is also apparent in that a larger region lighter than the surrounding region is found when an air pocket is present during a steam sterilization process. This can be seen, for example, comparing the chemical indicator 1020 with the lead carbonate chemical indicator 1220 in FIGS. 10 and 12, respectively. For certain embodiments, including any one of the above method embodiments, the first region has diameter of at least 2.5 cm when removal of the non-condensable gas was not sufficient under Air Leak Test Condition I. For certain of these embodiments, preferably the diameter is at least 3 cm, more preferably at least 3.5 cm. The first region is typically approximately circular or oval in shape, depending upon the particular shape of the air pocket or volume of non-condensable gas. The diameters indicated above refer to the largest diameter, since an oval shape is frequently encountered.

The test pack used in the above methods can be any process challenge device which restricts removal of a non-condensable gas from the area occupied by the chemical indicator. For certain embodiments, preferably the test pack is a vacuum test pack comprised of the chemical indicator sandwiched between porous sheets, for example, as described in U.S. Pat. No. 4,579,715, incorporated herein by reference.

Referring to FIG. 7, an exploded perspective view of the contents of vacuum test pack 100 is shown. Chemical indicator 220 with chemical indicator composition 240 coated thereon is sandwiched between porous sheet 200 and porous sheet 260. Porous sheets 200 and 260 can be made from various porous materials known in the art, e.g., in certain embodiments preferably paper, such as blotter paper, and may each be a single sheet or a stack of two or more sheets. Chemical indicator composition 240 is shown coated or printed in an X pattern, although other patterns, such as the diagonal pattern shown in chemical indicator 1120 of FIG. 11, illustrated as uniformly dark as a result of full exposure to steam, may be used as well. Chemical indicator composition 240 in FIG. 7 is illustrated in its light form, prior to exposure to steam. Chemical indicator composition 240A in chemical indicator 220A of FIG. 9 illustrates the composition in its darkened form, after full exposure to steam.

Substrates 180 and 280 illustrated in FIG. 7 have nonporous layers 160 and 300 attached (for example, laminated) thereto and are positioned with porous sheet 200 interposed between nonporous layer 160 and chemical indicator 220 and with porous sheet 260 between nonporous layer 300 and chemical indicator 220. Nonporous layers 160 and 300 may be plastic, metal sheeting, such as foil, or like material which prevents or restricts passage of non-condensable gas and steam from passing therethrough. Although shown as a laminate, nonporous layers 160 and 300 can consist of a single layer of nonporous material. The resulting stack of sheets is enclosed in a porous overwrap 120, which is secured with a tape 140, both of which are illustrated in FIG. 7.

Test pack 100 ready for use is illustrated in FIG. 8. In this test pack construction, removal of non-condensable gas from the area occupied by chemical indicator 220 and movement of steam into this area is restricted to the edges of porous sheets 200 and 260 after passing through porous overwrap 120. Tape 140 can be a chemical indicator tape, and for certain embodiments is the chemical indicator tape described herein.

For certain embodiments, including any one of the above method embodiments, the test pack is positioned in the most challenging area of the steam sterilizer for removing the non-condensable gas. In one example, the test pack is placed in the lowest area within sterilizer. In another example, the test pack is placed on or near the sterilizer drain. If the test pack is being used to conduct the Bowie-Dick Test, the test pack is positioned over the drain as recommended in standards such as ANSI/AAMI ST79:2006 (Comprehensive guide to steam sterilization and sterility assurance in health care facilities). In another example, the test pack is placed within an article to be sterilized or within a grouping of articles to be sterilized within the steam sterilizer.

Compositions described herein may also include a solvent for dispersing the various components of the composition, and in certain embodiments, preferably for dissolving the binder. Suitable solvents include alcohols, esters, ketones, and aromatic hydrocarbons. For certain embodiments, the solvent is preferably selected from the group consisting of n-propyl acetate, n-propyl alcohol, methanol, ethanol, 2-ethoxyethanol, butyl acetate, n-butanol, toluene, cyclohexanone, and a combination thereof. The compositions may be provided as chemical indicator inks, or the compositions may be coated onto a substrate and any solvent present evaporated, for example, by heating in an oven to provide a chemical indicator.

The compositions may include other additives, such as defoamers, flow aids, fillers, pigments, dyes, plasticizers, surfactants, and the like, so that when coated the compositions provide coatings having desirable properties. Such properties include uniform thickness, desired surface properties (glossy surface, mat surface, or the like), sufficient flexibility for bending without cracking, a particular starting color prior to exposure to steam sterilization process conditions, and the like, and combinations thereof.

As mentioned above, the color of the steam-exposed lead-free chemical indicator composition of the present invention ranges from brown to black, depending on formulation parameters. The pH of the substrate, the binder identity, the ratio of bismuth compound to lithium carbonate to sulfur, and the presence or absence of acid, can all affect the final color change of the lead-free chemical indicators on exposure to steam. Noting that some customers prefer the color change endpoint of a steam sterilization indicator to be black rather than brown, the inventors recognized that further addition of various dyes to the lead-free ink formulations described herein can effect a color change to black even when the ink formulation without added dye changes to brown. For example, addition of the blue dye, Hostaperm Blue, at final concentration of 0.05% liquid ink causes the original color of the ink to be pale green, rather than white, but effects a color change to black, rather than brown, after exposure to steam. Other dyes can be used provided they are soluble in the solvent system employed. To determine whether a dye used to obtain a black color when a brown color is normally obtained, the dye is dissolved in finished ink, mixed, coated onto substrate, exposed to steam for a desired steam sterilization cycle, and the original color and the final color are compared (e.g., brown to black).

Water-soluble dyes are often a different color when dispersed in organic solvents than they are when they are dissolved in water. Thus, water-soluble dyes are available that can be dispersed in the ink formulations of the present invention and will not change the original color of the ink substantially but will effect a black color change upon exposure to steam. Upon exposure, the water-soluble dye dissolves, becomes colored, and complements the brown color change of the indicator composition without added dye to provide a black appearance.

PH-indicating dyes are suitable for effecting a color change to black when the chemical indicator composition inherently turns brown. For example, bromocresol purple sodium salt, when added to an ink formulation at 0.01% of liquid ink, does not change substantially the color of the original printed ink, but effects a black color change on exposure to steam. Other pH indicators, such as bromothymol blue and phenol red, are suitable for the same purpose. While not intending to be bound, it is believed that the original color of the ink is not affected since the water-soluble pH indicator does not contact water during mixing of the dye with the chemical indicator ink solution that contains an organic solvent, such as alcohol solvents. Upon exposure to steam, however, and in the presence of base (e.g., lithium carbonate), the pH indicator dissolves and changes color, the final color of which, if complementary to brown, results in a black color change.

For certain embodiments, including any one of the chemical indicator composition embodiments, any one of the chemical indicator embodiments, or any one of the method embodiments described herein, the chemical indicator composition further comprises a dye which causes the color of the composition in the presence of steam to become black; wherein without the dye, the color of the composition in the presence of steam would be brown.

As indicated above, the chemical indicators described herein include a substrate. The substrate may be any substrate which remains intact and does not degrade when subjected to steam sterilization process conditions. Suitable substrates include paper without or with a saturant (e.g., rubber, natural or synthetic latex, a polymer, or the like), coated paper, cardboard, plastic sheeting, metalized sheeting, metal foil, nonwoven or woven fabrics, and the like.

For certain embodiments, including any one of the above chemical indicator embodiments and any one of the method embodiments, the chemical indicator is in the form of a Bowie-Dick indicator sheet. These are also known as Bowie-Dick Class 2 indicators. Such indicators are comprised of a sheet of material with the chemical indicator composition disposed thereon. The material may be nonporous or porous. In one embodiment, the sheet of material is porous paper, for example, kraft paper. The chemical indicator composition may be disposed on the sheet by various methods, including, for example, printing the composition, for example, in the form of an ink, onto the sheet or by applying a chemical indicator tape described herein to the sheet. The chemical indicator composition is preferably disposed over a sufficient area of the sheet to reveal the presence of an air pocket in a steam sterilizer. In one example, an 8.25 cm by 11.4 cm area of an 11.1 cm by 12.6 cm sheet is coated with the chemical indicator composition, such as illustrated with chemical indicators shown in FIGS. 7 through 12.

Alternatively, for certain embodiments, including any one of the above chemical indicator embodiments and any one of the method embodiments, except where the chemical indicator is in the form of a Bowie-Dick indicator sheet, the chemical indicator is in the form of an indicator strip. Indicator strips may be about 0.3 to about 2 centimeters wide by about 7 to 20 centimeters (cm) long, for example, about 1.25 cm by about 10 cm. The indicator strip includes the chemical indicator composition printed in the form of a stripe covering a portion or all of the strip. The substrate for the chemical indicator composition may be porous, such as paper, including, for example, craft paper, crepe paper, and the like, or may be nonporous, such as a polymeric film or plastic sheet, metallic sheet, such as foil, and the like.

Alternatively, for certain embodiments, including any one of the above chemical indicator embodiments and any one of the method embodiments, except where the chemical indicator is in the form of a Bowie-Dick indicator sheet or an indicator strip, the chemical indicator is in the form of a label; wherein the chemical indicator further comprises an adhesive layer on the major surface of the substrate opposite the major surface of the substrate upon which the chemical indicator composition is coated. For certain of these embodiments, the chemical indicator further comprises a liner covering the adhesive layer.

For certain embodiments, including any one of the above chemical indicator embodiments and any one of the method embodiments, the substrate of the chemical indicator is impregnated with a saturant.

For certain embodiments, including any one of the above chemical indicator embodiments and any one of the method embodiments, the substrate of the chemical indicator further includes a barrier layer, and the chemical indicator composition is coated on the barrier layer. For certain of these embodiments, the chemical indicator further comprises a low adhesion back-size layer covering the barrier layer and covering the chemical indicator composition coated on the barrier layer. Alternatively, the chemical indicator further comprising a barrier layer covering the major surface of the substrate and covering the chemical indicator composition coated on the at least a portion of the major surface of the substrate. For certain of these embodiments, the chemical indicator further comprises a low adhesion back-size layer covering the barrier layer.

For certain embodiments, including any one of the above chemical indicator embodiments and any one of the method embodiments, the chemical indicator further comprises an adhesive layer on the major surface of the substrate opposite the major surface of the substrate upon which the chemical indicator composition is coated.

For certain embodiments, including any one of the above chemical indicator embodiments and any one of the method embodiments, the chemical indicator is a tape.

For certain embodiments, the substrate is in the form of a tape. In one example, preferably the tape is comprised of a pressure sensitive adhesive on one side and any one of the composition embodiments described above on the opposite side. Preferably the tape is provided in roll form.

Referring to FIG. 13, in one embodiment, chemical indicator tape 1300 is illustrated in cross-section. Substrate 1310 is coated with chemical indicator composition 1340 on a portion of a first major surface and has adhesive layer 1320 covering at least a portion of the major surface on the side opposite composition 1340. Chemical indicator composition 1340 may be any one of the composition embodiments described herein. For certain embodiments, composition 1340 is coated on substrate 1310 by printing a chemical indicator composition described herein in the form of an ink. Substrate 1310 is preferably a paper, for example, kraft paper or crepe paper impregnated with a saturant. Saturants sufficiently resistant to steam may be used, for example, natural rubber and/or polymerized rosins without or with a pigment, for example zinc oxide and/or titanium oxide; styrene-butadiene polymers without or with rosin; acrylic polymer; a combination of acrylic polymer, styrene-butadiene polymer, and acrylonitrile polymer, and n-butyl acrylate-acrylonitrile-styrene terpolymer. The adhesive layer is preferably a water resistant pressure sensitive adhesive (PSA). PSAs which may be used for the adhesive layer include, for example, cross-linked acrylics, tackified rubber adhesives, for example, natural rubber, polyisoprene, styrene butadiene rubber, and the like.

Chemical indicator tape 1300 illustrated in FIG. 13 further includes barrier layer 1370 covering substrate 1310 and chemical indicator composition 1340. Low adhesion back-size layer 1390 covers barrier layer 1370. Materials which may be used for the barrier layer include, for example, acrylic polymers, urea-formaldehyde compositions, styrene butadiene rubbers, cellulose acetate, cellulose acetate propionate, cellulose acetate butyrate, ethyl cellulose, non-drying coconut oil alkyd, and acrylic modified alkyd. Materials which may be used for the low adhesion backsize layer or release layer include, for example, acrylic, urethane, and silicone polymers.

Referring to FIG. 14, in another embodiment, chemical indicator tape 1400 is illustrated in cross-section. Substrate 1410 is coated with chemical indicator composition 1440 on a portion of a first major surface and has adhesive layer 1420 covering at least a portion of the major surface on the side opposite composition 1440. Substrate 1410 is preferably a paper, for example, kraft paper or crepe paper impregnated with a saturant. Chemical indicator tape 1400 illustrated in FIG. 14 further includes saturant layer 1450 covering composition 1440, barrier layer 1470 covering substrate 1410 and saturant layer 1450, and low adhesion backsize layer 1490 covering barrier layer 1470. The adhesive, saturant, barrier, and low adhesion backsize layers described with respect to FIG. 13 may also be used here.

Referring to FIG. 15, in another embodiment, chemical indicator tape 1500 is illustrated in cross-section. Substrate 1510 is covered with barrier layer 1570 on a first major surface and has adhesive layer 1520 covering at least a portion of the major surface on the side opposite barrier layer 1570. Substrate 1510 is preferably a paper, for example, kraft paper or crepe paper impregnated with a saturant. Chemical indicator tape 1500 illustrated in FIG. 15 further includes chemical indicator composition 1540 coated on at least a portion of barrier layer 1570, and low adhesion backsize layer 1590 covering barrier layer 1570 and chemical indicator composition 1540. The adhesive, saturant, barrier, and low adhesion backsize layers described with respect to FIG. 13 may also be used here. For certain embodiments, the barrier layer 1570 is an acrylic polymer.

For certain alternative embodiments, the substrate is in the form of a rectangular or square sheet having an area on which the composition has been coated. In another alternative, the substrate is in the form of a bag or other wrapping with the composition coated onto a small area of the bag or wrapping.

Compositions described herein can be conveniently prepared by mixing the components of the binder, a solvent, the bismuth compound, the elemental sulfur, and the compound which makes the composition alkaline when exposed to water vapor at an elevated temperature. The mixing can be carried out using known mixing processes. In one example, the mixing is carried out in a ball mill wherein the particle size of the insoluble components (e.g., elemental sulfur, the compound which makes the composition alkaline, the bismuth compound) is reduced and the particles are dispersed. The binder and the solvent together may comprise about 50 to 97 percent by weight of the composition, and the elemental sulfur, the compound which makes the composition alkaline, and the bismuth compound in combination may comprise about 3 to about 50 percent by weight, preferably about 20 to about 25 percent by weight of the composition.

Compositions described herein may be coated onto the substrate using a variety of known coating methods including by a wire-wound rod (i.e., Meyer bar or Mayer rod) and various printing methods, including, for example, flexographic, rotogravure, and screen printing. The compositions may be applied in a pattern, for example, stripes, chevrons, or the like, to provide a visual contrast between areas of the indicator which will provide a color change after exposure to steam sterilization conditions and background areas of the indicator. Alternatively, the indicator may be coated without a pattern, such as by web coating techniques.

As indicated above, more than one substrate may be used in an indicator to provide desirable optical densities for use in multiple sterilization process conditions and for use as multiple classes of chemical indicators. Likewise, more than one composition may be coated and used in an indicator for the same purposes.

For certain embodiments, a film can be laminated onto the coated composition. Preferably the film is permeable to steam, although in certain embodiments steam may contact the coated composition through the substrate upon which the composition is coated.

Optical densities of the compositions are measured after the composition is coated onto a substrate and any solvent evaporated from the composition. Known devices for measuring optical densities of a surface may be used, such as a densitometer.

EXEMPLARY EMBODIMENTS

Exemplary embodiments of the present invention include:
1. A chemical indicator composition comprising:
    a) a bismuth (III) compound selected from the group consisting of bismuth (III) oxide and a bismuth (III) compound comprising at least one organic group which includes 2 to 20 carbon atoms;
    b) elemental sulfur; and
    c) a compound which makes the composition alkaline when exposed to water vapor at an elevated temperature.
2. The composition of embodiment 1, wherein the bismuth (III) compound is a bismuth (III) compound comprising at least one organic group which includes 2 to 20 carbon atoms.
3. The composition of embodiment 1 or embodiment 2, wherein the bismuth (III) compound is selected from the group consisting of bismuth subsalicylate, bismuth gallate, bismuth subgallate, bismuth pyrogallate, bismuth acetate, bismuth citrate, bismuth potassium citrate, ammonium bismuth citrate, bismuth lactate, bismuth oxalate, bismuth benzoate, bismuth formate, bismuth propionate, bismuth butyrate, bismuth pivalate, 2-propylpentanoic acid bismuth salt, bismuth ascorbate, bismuth diethyldithiocarbamate, bismuth dimethyldithiocarbamate, bismuth 2-ethylhexanoate, bismuth neodecanoate, bismuth oleate, bismuth gluconate, bismuth potassium D-gluconate, bismuth naphtholate, naphthenic acid bismuth salt, bismuth triglycollamate, bismuth sodium triglycollamate, bismuth succinate, bismuth maleate, bismuth tartrate, bismuth sodium tartrate, bismuth potassium tartrate, bismuth tannate, 3-camphocarboxylic acid bismuth salt, bismuth ethylcamphorate, bismuth oxyquinoline, 2-oxo-3-bornanecarboxylic acid bismuth salt, bismuth valproate, and a combination thereof.
4. The composition of embodiment 3, wherein the bismuth (III) compound is bismuth subsalicylate.
5. The composition of embodiment 1, wherein the bismuth (III) compound is bismuth (III) oxide.
6. The composition of any one of embodiments 1 through 5, wherein the compound which makes the composition alkaline has a solubility in water at 100° C. of not more than 1 gram per 100 cubic centimeters of water.
7. The composition of any one of embodiments 1 through 6, wherein the compound which makes the composition alkaline is selected from the group consisting of lithium carbonate, magnesium carbonate, calcium carbonate, barium carbonate, calcium hydroxide, magnesium hydroxide, or a combination thereof.
8. The composition of embodiment 7, wherein the compound which makes the composition alkaline is lithium carbonate.
9. The composition of any one of embodiment 1 through 8, further comprising a binder.
10. The composition of embodiment 9, wherein the binder comprises a polymer comprising acid groups, and wherein the binder has an acid number of at least 7.
11. The composition of any one of embodiments 1 through 10, further comprising at least one acid.
12. The composition of embodiment 11, wherein the acid is present in an amount of at least 0.005 equivalents acid per equivalent of the compound which makes the composition alkaline.
13. The composition of any one of embodiments 1 through 12, wherein when exposed to a first condition selected from the group consisting of steam at a temperature of 134° C. for 2 minutes and steam at a temperature of 121° C. for 10 minutes, the composition undergoes a change in optical density resulting in an optical density of at least 0.4, and wherein when instead exposed to a second condition selected from the group consisting of steam at a temperature of 134° C. for 0.5 minutes and steam at a temperature of 121° C. for 3 minutes, any change in optical density is at least 0.3 optical density units less than when exposed to the first condition.

14. The composition of embodiment 13, wherein when exposed to the first condition, the composition undergoes a change in optical density resulting in an optical density of at least 0.5.

15. The composition of any one of embodiments 1 through 14, wherein when exposed to a first condition selected from the group consisting of steam at a temperature of 134° C. for 2 minutes and steam at a temperature of 121° C. for 10 minutes, the composition changes color to brown or black.

16. The composition of embodiment 13 or embodiment 14, wherein when exposed to the first condition the composition undergoes a change in optical density resulting in an optical density of at least 1.0, and wherein the first condition is steam at a temperature of 121° C. for 10 minutes.

17. The composition of any one of embodiments 1 through 16, wherein when exposed to steam at 134° C. for 3.5 minutes the composition undergoes a change in optical density resulting in an optical density of at least 1.0, and wherein when instead exposed to steam at a temperature of 132° C. for 2.5 minutes, any change in optical density is at least 0.3 optical density units less than when exposed steam at 134° C. for 3.5 minutes.

18. The composition of any one of embodiments 1 through 17, wherein the bismuth (III) compound and the elemental sulfur are present in a weight ratio of not more than 2:3 and not less than 0.5:3; and wherein the elemental sulfur and the compound which makes the composition alkaline are present in a weight ratio of not more than 1:1 and not less than 1:5.

19. A chemical indicator comprising:
 a substrate and a chemical indicator composition coated on at least a portion of a major surface of the substrate, the composition comprising:
  a) a bismuth (III) compound selected from the group consisting of bismuth (III) oxide and a bismuth (III) compound comprising at least one organic group which includes 2 to 20 carbon atoms;
  b) elemental sulfur; and
  c) a compound which makes the composition alkaline when exposed to water vapor at an elevated temperature.

20. The indicator of embodiment 19, wherein the bismuth (III) compound is a bismuth (III) compound comprising at least one organic group which includes 2 to 20 carbon atoms.

21. The indicator of embodiment 19 or embodiment 20, wherein the bismuth (III) compound is selected from the group consisting of bismuth subsalicylate, bismuth gallate, bismuth subgallate, bismuth pyrogallate, bismuth acetate, bismuth citrate, bismuth potassium citrate, ammonium bismuth citrate, bismuth lactate, bismuth oxalate, bismuth benzoate, bismuth formate, bismuth propionate, bismuth butyrate, bismuth pivalate, 2-propylpentanoic acid bismuth salt, bismuth ascorbate, bismuth diethyldithiocarbamate, bismuth dimethyldithiocarbamate, bismuth 2-ethylhexanoate, bismuth neodecanoate, bismuth oleate, bismuth gluconate, bismuth potassium D-gluconate, bismuth naphtholate, naphthenic acid bismuth salt, bismuth triglycollamate, bismuth sodium triglycollamate, bismuth succinate, bismuth maleate, bismuth tartrate, bismuth sodium tartrate, bismuth potassium tartrate, bismuth tannate, 3-camphocarboxylic acid bismuth salt, bismuth ethylcamphorate, bismuth oxyquinoline, 2-oxo-3-bornanecarboxylic acid bismuth salt, bismuth valproate, and a combination thereof.

22. The indicator of embodiment 21, wherein the bismuth (III) compound is bismuth subsalicylate.

23. The indicator of embodiment 19, wherein the bismuth (III) compound is bismuth (III) oxide.

24. The indicator of any one of embodiments 19 through 23, wherein the compound which makes the composition alkaline has a solubility in water at 100° C. of not more than 1 gram per 100 cubic centimeters of water.

25. The indicator of any one of embodiments 19 through 24, wherein the compound which makes the composition alkaline is selected from the group consisting of lithium carbonate, magnesium carbonate, calcium carbonate, barium carbonate, calcium hydroxide, magnesium hydroxide, or a combination thereof.

26. The indicator of embodiment 25, wherein the compound which makes the composition alkaline is lithium carbonate.

27. The indicator of any one of embodiment 19 through 26, wherein the composition further comprises a binder.

28. The indicator of embodiment 27, wherein the binder comprises a polymer comprising acid groups, and wherein the binder has an acid number of at least 7.

29. The indicator of any one of embodiments 19 through 28, wherein the composition further comprises at least one acid.

30. The indicator of embodiment 29, wherein the acid is present in an amount of at least 0.005 equivalents acid per equivalent of the compound which makes the composition alkaline.

31. The indicator of any one of embodiments 19 through 30, wherein when exposed to a first condition selected from the group consisting of steam at a temperature of 134° C. for 2 minutes and steam at a temperature of 121° C. for 10 minutes, the composition undergoes a change in optical density resulting in an optical density of at least 0.4, and wherein when instead exposed to a second condition selected from the group consisting of steam at a temperature of 134° C. for 0.5 minutes and steam at a temperature of 121° C. for 3 minutes, any change in optical density is at least 0.3 optical density units less than when exposed to the first condition.

32. The indicator of embodiment 31, wherein when exposed to the first condition, the composition undergoes a change in optical density resulting in an optical density of at least 0.5.

33. The indicator of any one of embodiments 19 through 32, wherein the substrate is a paper with a pH of not more than 6.

34. The indicator of embodiment 33, wherein when exposed to steam at a temperature of 134° C. for 3.5 minutes, the composition undergoes a change in optical density resulting in an optical density of at least 0.8, and wherein when instead exposed to steam at a temperature of 132° C. for 2.5 minutes, any change in optical density is at least 0.4 optical density units less than when exposed to steam at the temperature of 134° C. for 3.5 minutes.

35. The indicator of embodiment 33, wherein when exposed to steam at a temperature of 121° C. for 10 minutes, the composition undergoes a change in optical density resulting in an optical density of at least 0.8, and wherein when instead exposed to steam at a temperature of 121° C. for 3 minutes, any change in optical density is at least 0.4 optical density units less than when exposed to steam at the temperature of 121° C. for 10 minutes.

36. The indicator of any one of embodiments 19 through 32, wherein the substrate is a paper with a pH greater than 6.

37. The indicator of embodiment 36, wherein when exposed to steam at a temperature of 134° C. for 2.0 minutes, the composition undergoes a change in optical density resulting in an optical density of at least 0.8, and wherein when instead exposed to steam at a temperature of 134° C. for 0.5 minutes, any change in optical density is at least 0.4 optical density units less than when exposed to steam at the temperature of 134° C. for 2.0 minutes.

38. The indicator of any one of embodiments 19 through 37, wherein when exposed to a first condition selected from the group consisting of steam at a temperature of 134° C. for 2 minutes and steam at a temperature of 121° C. for 10 minutes, the composition changes color to brown or black.
39. The indicator of any one of embodiments 19 through 38, wherein when exposed to steam at a temperature of 121° C. for 10 minutes, the composition undergoes a change in optical density resulting in an optical density of at least 1.0.
40. The indicator of any one of embodiments 19 through 39, wherein when exposed to steam at 134° C. for 3.5 minutes the composition undergoes a change in optical density resulting in an optical density of at least 1.0, and wherein when instead exposed to steam at a temperature of 132° C. for 2.5 minutes, any change in optical density is at least 0.3 optical density units less than when exposed steam at 134° C. for 3.5 minutes.
41. The indicator of any one of embodiments 19 through 40, wherein the bismuth (III) compound and the elemental sulfur are present in the composition in a weight ratio of not more than 2:3 and not less than 0.5:3; and wherein the elemental sulfur and the compound which makes the composition alkaline are present in a weight ratio of not more than 1:1 and not less than 1:5.
42. A chemical indicator composition comprising:
    a) a bismuth (III) compound;
    b) elemental sulfur;
    c) a compound which makes the composition alkaline when exposed to water vapor at an elevated temperature; and
    d) at least one acid other than any acid present in the bismuth (III) compound.
43. The composition of embodiment 42, wherein the acid is present in an amount of at least 0.005 equivalents acid per equivalent of the compound which makes the composition alkaline.
44. The composition of embodiment 42 and embodiment 43, wherein the acid is selected from the group consisting of 2-hydroxybenzoic acid, benzoic acid, p-toluenesulphonic acid, phenylacetic acid, citric acid, suberic acid, and a combination thereof.
45. The composition of any one of embodiments 42, 43, and 44, wherein the bismuth (III) compound and the elemental sulfur are present in a weight ratio of not more than 2:3 and not less than 0.5:3; and wherein the elemental sulfur and the compound which makes the composition alkaline are present in a weight ratio of not more than 1:1 and not less than 1:5.
46. The composition of any one of embodiments 42 through 45, wherein the compound which makes the composition alkaline has a solubility in water at 100° C. of not more than 1 gram per 100 cubic centimeters of water.
47. The composition of any one of embodiments 42 through 46, wherein the compound which makes the composition alkaline is selected from the group consisting of lithium carbonate, magnesium carbonate, calcium carbonate, barium carbonate, calcium hydroxide, magnesium hydroxide, or a combination thereof.
48. The composition of embodiment 47, wherein the compound which makes the composition alkaline is lithium carbonate.
49. The composition of any one of embodiment 42 through 48 further comprising a binder.
50. The composition of embodiment 49, wherein the binder comprises a polymer comprising acid groups, and wherein the binder has an acid number of at least 7.
51. The composition of any one of embodiments 42 through 50, wherein when exposed to a first condition selected from the group consisting of steam at a temperature of 134° C. for 2 minutes and steam at a temperature of 121° C. for 10 minutes, the composition undergoes a change in optical density resulting in an optical density of at least 0.4, and wherein when instead exposed to a second condition selected from the group consisting of steam at a temperature of 134° C. for 0.5 minutes and steam at a temperature of 121° C. for 3 minutes, any change in optical density is at least 0.3 optical density units less than when exposed to the first condition.
52. The composition of embodiment 51, wherein when exposed to the first condition, the composition undergoes a change in optical density resulting in an optical density of at least 0.5.
53. The composition of any one of embodiments 42 through 52, wherein when exposed to a first condition selected from the group consisting of steam at a temperature of 134° C. for 2 minutes and steam at a temperature of 121° C. for 10 minutes, the composition changes color to brown or black.
54. The composition of embodiment 51 or embodiment 52, wherein when exposed to the first condition the composition undergoes a change in optical density resulting in an optical density of at least 1.0, and wherein the first condition is steam at a temperature of 121° C. for 10 minutes.
55. A chemical indicator comprising:
    a substrate and the chemical indicator composition of any one of embodiments 42 through 54 coated on at least a portion of a major surface of the substrate.
56. The indicator of embodiment 55, wherein the substrate is a paper with a pH of not more than 6.
57. The indicator of embodiment 56, wherein when exposed to steam at a temperature of 134° C. for 3.5 minutes, the composition undergoes a change in optical density resulting in an optical density of at least 0.8, and wherein when instead exposed to steam at a temperature of 132° C. for 2.5 minutes, any change in optical density is at least 0.4 optical density units less than when exposed to steam at the temperature of 134° C. for 3.5 minutes.
58. The indicator of embodiment 56, wherein when exposed to steam at a temperature of 121° C. for 10 minutes, the composition undergoes a change in optical density resulting in an optical density of at least 0.8, and wherein when instead exposed to steam at a temperature of 121° C. for 3 minutes, any change in optical density is at least 0.7 optical density units less than when exposed to steam at the temperature of 121° C. for 10 minutes.
59. The indicator of embodiment 55, wherein the substrate is a paper with a pH greater than 6.
60. The indicator of embodiment 59, wherein when exposed to steam at a temperature of 134° C. for 2.0 minutes, the composition undergoes a change in optical density resulting in an optical density of at least 0.8, and wherein when instead exposed to steam at a temperature of 134° C. for 0.5 minutes, any change in optical density is at least 0.4 optical density units less than when exposed to steam at the temperature of 134° C. for 2.0 minutes.
61. A method of determining the effectiveness of a steam sterilization process, the method comprising:
    providing a chemical indicator of any one of embodiments 19 through 41, and 55 through 60;
    placing the chemical indicator in a steam sterilization chamber;
    exposing the chemical indicator to steam at a temperature of at least 121° C.; and
    determining an optical density of the chemical indicator.
62. The method of embodiment 61, further comprising placing an article to be sterilized along with the chemical indicator in the sterilization chamber.

63. The method of embodiment 61 or embodiment 62, further comprising determining whether or not sterilization conditions were met in the sterilization chamber.

64. A method of making a chemical indicator having a targeted change in optical density when exposed to a steam sterilization process condition; the method comprising:

selecting at least one optical density-controlling component for including in the chemical indicator; wherein the optical density-controlling component is selected from the group consisting of at least one acid; at least one polymer comprising acid groups, the polymer having an acid number of at least 7; at least one binder compound which can produce an acid when exposed to water vapor at an elevated temperature; a paper having a pH not more than 6, a paper having a pH greater than 6; and a combination thereof;

preparing a chemical indicator composition comprising:
a) a bismuth (III) compound;
b) elemental sulfur;
c) a compound which makes the composition alkaline when exposed to water vapor at an elevated temperature;
d) a binder; and, if selected,
e) the at least one acid, the at least one polymer comprising acid groups, the at least one binder compound, or a combination thereof; wherein, if selected, the at least one polymer, the at least one binder compound, or a combination thereof comprises at least a portion of the binder; and coating the composition on at least a portion of a major surface of a substrate;

wherein, if selected, the paper having a pH not more than 6, the paper having a pH greater than 6, or both are the substrate.

65. The method of embodiment 64; wherein the at least one polymer comprising acid groups is selected.

66. The method of embodiment 65, wherein when exposed to steam at a temperature of 134° C. for 3.5 minutes, the composition undergoes a change in optical density resulting in an optical density of at least 0.8, and wherein when instead exposed to steam at a temperature of 132° C. for 2.5 minutes, any change in optical density is at least 0.3 optical density units less than when exposed to steam at the temperature of 134° C. for 3.5 minutes.

67. The method of embodiment 64 or embodiment 65, wherein the at least one acid is selected.

68. The method of embodiment 67, wherein when exposed to steam at a temperature of 134° C. for 2.0 minutes, the composition undergoes a change in optical density resulting in an optical density of at least 0.6, and wherein when instead exposed to steam at a temperature of 134° C. for 0.5 minutes, any change in optical density is at least 0.5 optical density units less than when exposed to steam at the temperature of 134° C. for 2.0 minutes.

69. The method of any one of embodiments 64, 65, and 67, wherein the paper having a pH not more than 6 is selected.

70. The method of embodiment 69, wherein when exposed to steam at a temperature of 134° C. for 3.5 minutes, the composition undergoes a change in optical density resulting in an optical density of at least 1.0, and wherein when instead exposed to steam at a temperature of 132° C. for 2.5 minutes, any change in optical density is at least 0.4 optical density units less than when exposed to steam at the temperature of 134° C. for 3.5 minutes.

71. The method of embodiment 69 or embodiment 70, wherein when exposed to steam at a temperature of 121° C. for 10 minutes, the composition undergoes a change in optical density resulting in an optical density of at least 1.0, and wherein when instead exposed to steam at a temperature of 121° C. for 3.0 minutes, any change in optical density is at least 0.7 optical density units less than when exposed to steam at the temperature of 121° C. for 10 minutes.

72. The method of any one of embodiments 64, 65, and 67, wherein the paper having a pH greater than 6 is selected.

73. The method of embodiment 72, wherein when exposed to steam at a temperature of 134° C. for 2.0 minutes, the composition undergoes a change in optical density resulting in an optical density of at least 0.8, and wherein when instead exposed to steam at a temperature of 134° C. for 0.5 minutes, any change in optical density is at least 0.4 optical density units less than when exposed to steam at the temperature of 134° C. for 2.0 minutes.

74. The method of any one of embodiments 64 through 73, wherein the bismuth (III) compound is selected from the group consisting of bismuth (III) oxide and a bismuth (III) compound comprising at least one organic group which includes 2 to 20 carbon atoms.

75. The method of embodiment 74, wherein the bismuth (III) compound is a bismuth (III) compound comprising at least one organic group which includes 2 to 20 carbon atoms.

76. The method of embodiment 74 or embodiment 75, wherein the bismuth (III) compound is selected from the group consisting of bismuth subsalicylate, bismuth gallate, bismuth subgallate, bismuth pyrogallate, bismuth acetate, bismuth citrate, bismuth potassium citrate, ammonium bismuth citrate, bismuth lactate, bismuth oxalate, bismuth benzoate, bismuth formate, bismuth propionate, bismuth butyrate, bismuth pivalate, 2-propylpentanoic acid bismuth salt, bismuth ascorbate, bismuth diethyldithiocarbamate, bismuth dimethyldithiocarbamate, bismuth 2-ethylhexanoate, bismuth neodecanoate, bismuth oleate, bismuth gluconate, bismuth potassium D-gluconate, bismuth naphtholate, naphthenic acid bismuth salt, bismuth triglycollamate, bismuth sodium triglycollamate, bismuth succinate, bismuth maleate, bismuth tartrate, bismuth sodium tartrate, bismuth potassium tartrate, bismuth tannate, 3-camphocarboxylic acid bismuth salt, bismuth ethylcamphorate, bismuth oxyquinoline, 2-oxo-3-bornanecarboxylic acid bismuth salt, bismuth valproate, and a combination thereof.

77. The method of embodiment 76, wherein the bismuth (III) compound is bismuth subsalicylate.

78. The method of embodiment 74, wherein the bismuth (III) compound is bismuth (III) oxide.

79. The method of any one of embodiments 74 through 78, wherein the binder has an acid number of 0 to less than 7.

80. The method of embodiment 79, wherein when exposed to steam at a temperature of 134° C. for 2.0 minutes, the composition undergoes a change in optical density resulting in an optical density of at least 0.8, and wherein when instead exposed to steam at a temperature of 134° C. for 0.5 minutes, any change in optical density is at least 0.5 optical density units less than when exposed to steam at the temperature of 134° C. for 2.0 minutes.

81. The method of any one of embodiments 64 through 80, wherein the compound which makes the composition alkaline has a solubility in water at 100° C. of not more than 1 gram per 100 cubic centimeters of water.

82. The method of any one of embodiments 64 through 81, wherein the compound which makes the composition alkaline is selected from the group consisting of lithium carbonate, magnesium carbonate, calcium carbonate, barium carbonate, calcium hydroxide, magnesium hydroxide, or a combination thereof.

83. The method of embodiment 82, wherein the compound which makes the composition alkaline is lithium carbonate.

84. The method of any one of embodiments 64 through 83, wherein the bismuth (III) compound and the elemental sulfur are present in the composition in a weight ratio of not more than 2:3 and not less than 0.5:3; and wherein the elemental sulfur and the compound which makes the composition alkaline are present in a weight ratio of not more than 1:1 and not less than 1:5.

85. A method of determining effectiveness of a steam sterilization process, the method comprising determining whether or not sufficient removal of non-condensable gas from a steam sterilizer has occurred by:

providing a chemical indicator according to any one of embodiments 19 through 41 and 55 through 60; wherein the chemical indicator is positioned within a test pack; and wherein the chemical indicator composition of the chemical indicator is located at least in an area including the center of the test pack, at least in an area at or near the edges of the test pack, and at least in an area between the edges and center of the test pack;

positioning the test pack within the steam sterilizer;

exposing the test pack to the steam sterilization process; and examining the chemical indicator composition to determine the presence or absence of a first region distinctly lighter than a second surrounding region, the first region comprising a central zone and a peripheral zone surrounding the central zone and adjacent the second surrounding region; wherein both the central zone and the peripheral zone are distinctly lighter than the second surrounding region;

wherein the presence of the first region distinctly lighter than the second surrounding region is indicative of insufficient removal of non-condensable gas, and the absence of the first region distinctly lighter than the second surrounding region is indicative of sufficient removal of non-condensable gas.

86. The method of embodiment 85, wherein examining the chemical indicator composition is carried out visually.

87. The method of embodiment 85 or embodiment 86, wherein examining the chemical indicator composition is carried out photometrically.

88. The method of embodiment 87, wherein optical density of the chemical indicator composition in the central zone and optical density of the chemical indicator composition in the area at or near the edges of the test pack within the second surrounding region are measured and differ from each other by at least 0.30 optical density units when removal of the non-condensable gas is not sufficient under Air Leak Test Condition I; and wherein the optical densities differ from each other by not more than 0.05 optical density units when removal of the non-condensable gas is sufficient.

89. The method of embodiment 87 or embodiment 88, wherein optical density of the chemical indicator composition in the peripheral zone and optical density of the chemical indicator composition in the area at or near the edges of the test pack within the second surrounding region are measured and differ from each other by at least 0.15 optical density units when removal of the non-condensable gas is not sufficient under Air Leak Test Condition I; and wherein the optical densities differ from each other by less than 0.05 optical density units when removal of the non-condensable gas is sufficient.

90. The method of any one of embodiments 85 through 89, wherein the first region has a diameter of at least 2.5 cm when removal of the non-condensable gas is not sufficient under Air Leak Test Condition I.

91. The method of any one of embodiments 85 through 90, wherein the test pack is positioned in the most challenging area of the steam sterilizer for removing the non-condensable gas.

92. The chemical indicator according to any one of embodiments 19 through 41 and 55 through 60 or the method of any one of embodiments 61 through 91, wherein the chemical indicator is in the form of a Bowie-Dick indicator sheet.

93. The chemical indicator according to any one of embodiments 19 through 41 and 55 through 60 or the method of any one of embodiments 61 through 91, wherein the chemical indicator is in the form of an indicator strip.

94. The chemical indicator according to any one of embodiments 19 through 41 and 55 through 60 or the method of any one of embodiments 61 through 91, wherein the chemical indicator is in the form of a label; wherein the chemical indicator further comprises an adhesive layer on the major surface of the substrate opposite the major surface of the substrate upon which the chemical indicator composition is coated.

95. The chemical indicator of embodiment 94 or the method of embodiment 94, further comprising a liner covering the adhesive layer.

96. The chemical indicator of any one of embodiments 19 through 41 and 55 through 60 or the method of any one of embodiments 61 through 91, wherein the substrate is impregnated with a saturant.

97. The chemical indicator of any one of embodiments 19 through 41, 55 through 60, and 96 or the method of any one of embodiments 61 through 90 and 96, wherein the substrate further includes a barrier layer, and the chemical indicator composition is coated on the barrier layer.

98. The chemical indicator of any one of embodiments 19 through 41, 55 through 60, and 96 or the method of any one of embodiments 61 through 90 and 96, further comprising a barrier layer covering the major surface of the substrate and covering the chemical indicator composition coated on the at least a portion of the major surface of the substrate.

99. The chemical indicator of embodiment 98 or the method of embodiment 98, further comprising a low adhesion back-size layer covering the barrier layer.

100. The chemical indicator of embodiment 97 or the method of embodiment 97, further comprising a low adhesion back-size layer covering the barrier layer and covering the chemical indicator composition coated on the barrier layer.

101. The chemical indicator of any one of embodiments 19 through 41, 55 through 60, and 96 through 100 or the method of any one of embodiments 61 through 90 and 96 through 100, further comprising an adhesive layer on the major surface of the substrate opposite the major surface of the substrate upon which the chemical indicator composition is coated.

102. The chemical indicator of any one of embodiments 19 through 41, 55 through 60, and 96 through 101 or the method of any one of embodiments 61 through 90 and 96 through 101, wherein the chemical indicator is a tape.

103. The chemical indicator composition of any one of the preceding chemical indicator composition embodiments, the chemical indicator of any one of the preceding chemical indicator embodiments, or the method of any one of the preceding method embodiments, wherein the chemical indicator composition further comprises a dye which causes the color of the composition in the presence of steam to become black; wherein without the dye, the color of the composition in the presence of steam would be brown.

Objects and advantages of this invention are further illustrated by the following examples, but the particular materials and amounts thereof recited in these examples, as well as other conditions and details, should not be construed to unduly limit this invention.

EXAMPLES

Milling Procedure

Unless otherwise indicated, compositions in Examples 1-24 were milled for 90 minutes in a Hockmeyer 1/16 basket mill or for 120 minutes using a Hockmeyer Micromill. The median particle size was about 2-2.5 micrometers with a standard deviation of about 1.5 micrometers. Thus, all samples had the same particle size distribution.

Air Leak Test Condition I

A steam sterilizer (AMSCO 3013 Steam Sterilizer) equipped with a Whitey Micrometering Valve (SS-22RS4 3000 PSI) connected to a rear port was used. In vacuum mode, air was pulled into the sterilization chamber of the AMSCO 3013 at a rate that was dependent on the differential between atmospheric pressure and the vacuum level in the sterilizer. An AMSCO 3013 4-Pulse prevacuum cycle was used, during which the level of vacuum varied while the 4 vacuum pulses were occurring during the Preconditioning Phase, and the amount of air going into the chamber varied with the vacuum level.

The micrometering valve can be set to different positions to allow different levels of air to leak into the chamber. When the valve is tightened to a more closed position, less air will leak into the chamber and when the valve is opened to a greater degree, more air will leak into the chamber. One way to characterize how far the micrometering valve has been opened and, therefore, the amount of air leakage is to determine the Air Leak Rate, using the AMSCO 3013's Air leak Test. This test was carried out as follows:

Step 1: Steam was allowed to flow through the chamber for one minute.

Step 2: After the purge phase (Step 1), a vacuum was pulled in the chamber for one minute and then down to 254 millimeters (mm) (10 inches) mercury (Hg) (0.034 MPa).

Steps 3-5: A steam pulse charge phase was begun and the chamber was charged to 0.28 MPa (26 psig), followed by one more vacuum pulse (to 254 mm Hg). This step was repeated 2 more times.

Step 6: The chamber was charged with steam to 132° C. Once temperature was reached, evacuation was begun.

Step 7: The chamber was exhausted and a vacuum was pulled in the chamber for 10 minutes.

Step 8: After the 10 minute time period, the chamber was allowed to stabilize for 2 minutes. This phase ensured a constant vacuum level after the vacuum system has been turned off. The sterilizer chamber was sealed so that no steam or gas could enter the chamber from the jacket or steam supply and no steam or gas could leave through the drain. The only point that air could deliberately enter the chamber was through the micrometering valve. Prior to conducting this test, an air leak test should be conducted to ensure that the steam sterilizer is operating without or with minimal air leaks, except for the deliberate air leak through the valve, since this test will detect all sources of air leaking into the sterilizer chamber, for example, a faulty door gasket. The vacuum pressure in mm Hg was measured.

Step 9: During this leak test phase, the chamber remained idle for 10 minutes at which time a second vacuum pressure measurement was made in mm Hg. A calculation was made to obtain the mm Hg change per minute.

Settings of choice for the micrometering valve for assessing detection of air pockets with Bowie-Dick test packs in the Amsco 3013 can provide a pressure change of 3 to 20 mm Hg per minute.

It is noted that the Amsco 3013 has a volume of approximately 108 liters. If a steam sterilizer of this type with a larger chamber were used, it should be noted that the pressure change per minute that would allow the same amount of air into the sterilizer would have a lesser number for the mm Hg per minute. From the Ideal Gas law it should be recognized that pressure and volume are inversely proportional.

It is also noted that the presently disclosed methods can be used to detect a wide range of air leaks including all sources of air leaking into the sterilizer chamber, such as through a faulty door gasket, and the presently disclosed methods are not limited to the above air leak test condition.

Example 1

Bismuth Subgallate with Methyl/n-Butyl Methacrylate Copolymer Binder

A binder solution was prepared by mixing 100 g methyl/n-butyl methacrylate copolymer (ELVACITE 2013, acid number=5, available from Lucite International, Cordova, Tenn.) with 261.6 g n-propyl acetate and 175.4 g n-propyl alcohol. The mixture was rolled overnight in a jar to give a homogeneous solution.

To the binder solution was added 21.28 g bismuth subgallate (Alfa Aesar, Ward Hill, Mass.), 64 g elemental sulfur (Akrochem, Akron, Ohio), and 85.2 g lithium carbonate (J. T. Baker, Phillipsburg, N.J.). The resulting mixture was milled using Zirstar zirconium oxide/yttrium oxide 1 mm beads (GEMCO, Atlanta, Ga.) in a Hockmeyer 1/16 basket mill (Hockmeyer Equipment Corporation, Elizabeth City, N.C.) for 90 minutes. The samples were coated onto white index paper, grade 5515-138 (Monadnock Paper Mills, Bennington, N.H.) using a #22 Meyer Bar (rod wound with 0.56 millimeter or 22 mils diameter wire). The coated papers were dried at 50° C. for 5 minutes, cut into approximately 0.64 cm (0.25 inch) by 3.8 cm (1.5 inch) strips, and then exposed to steam in a Joslyn resistometer at 121° C., 132° C., and 134° C. for various time periods. The optical density (OD) of each exposed sample was measured using a Macbeth RD917 densitometer using a white filter. Results are reported in Table 1.

TABLE 1

Bismuth subgallate/sulfur/lithium carbonate/ELVACITE 2013

| Time (min) | 121° C. OD | 132° C. OD | 134° C. OD |
| --- | --- | --- | --- |
| 0.5 | — | — | 0.21 |
| 2 | — | — | 0.57 |
| 2.5 | — | 0.63 | — |
| 3 | 0.40 | — | — |
| 3.5 | — | — | 0.96 |
| 10 | 1.24 | — | — |

Optical densities greater than 0.4 were found for 134° C., 2 min and 121° C., 10 min cycles and a difference of greater than 0.3 OD units was found between these values and optical densities for samples exposed at 134° C., 30 sec and 121° C., 3 min, respectively.

Example 2

Bismuth Subsalicylate with Methyl/n-Butyl methacrylate Copolymer Binder

A binder solution was prepared by mixing 100 g methyl/n-butylmethacrylate copolymer (ELVACITE 2013, acid number=5, available from Lucite International, Cordova, Tenn.) with 261.6 g n-propyl acetate and 175.4 g n-propyl alcohol. The mixture was rolled overnight in a jar to give a homogeneous solution.

To the binder solution was added 21.28 g bismuth subsalicylate (Alfa Aesar, Ward Hill, Mass.), 64 g elemental sulfur (Akrochem, Akron, Ohio), and 85.2 g lithium carbonate (J. T. Baker, Phillipsburg, N.J.). The resulting mixture was milled using Zirstar zirconium oxide/yttrium oxide 1 mm beads (GEMCO, Atlanta, Ga.) in a Hockmeyer 1/16 basket mill (Hockmeyer Equipment Corporation, Elizabeth City, N.C.) for 90 minutes. Samples were coated onto white index paper, grade 5515-138 (Monadnock Paper Mills, Bennington, N.H.) using a #22 Meyer Bar. The coated paper was dried at 50° C. for 5 minutes, cut into approximately 0.64 cm (0.25 inch) by 3.8 cm (1.5 inch) strips, and then exposed to steam in a Joslyn resistometer at 121° C., 132° C., and 134° C. for various time periods. The optical density (OD) of each exposed sample was measured using a Macbeth RD917 densitometer using a white filter. Results of the experiment are reported in Table 2.

TABLE 2

| Bismuth subsalicylate/sulfur/lithium carbonate/ELVACITE 2013 | | | |
|---|---|---|---|
| Time (min) | 121° C. OD | 132° C. OD | 134° C. OD |
| 0.5 | — | — | 0.19 |
| 2 | — | — | 1.00 |
| 2.5 | — | 1.12 | — |
| 3 | 0.33 | — | — |
| 3.5 | — | — | 1.24 |
| 10 | 1.21 | — | — |

Optical densities greater than 0.4 were found for 134° C., 2 min and 121° C., 10 min cycles and a difference of greater than 0.3 OD units was found between these values and optical densities for samples exposed at 134° C., 30 sec and 121° C., 3 min, respectively.

Example 3

Bismuth Subsalicylate with Poly(methyl methacrylate) Binder

A binder solution was prepared by mixing 100 g poly(methyl methacrylate) (ELVACITE 2008, acid number=9, available from Lucite International, Cordova, Tenn.) with 261.6 g n-propyl acetate and 175.4 g n-propyl alcohol. The mixture was rolled overnight in a jar to give a homogeneous solution.

Figure 2:
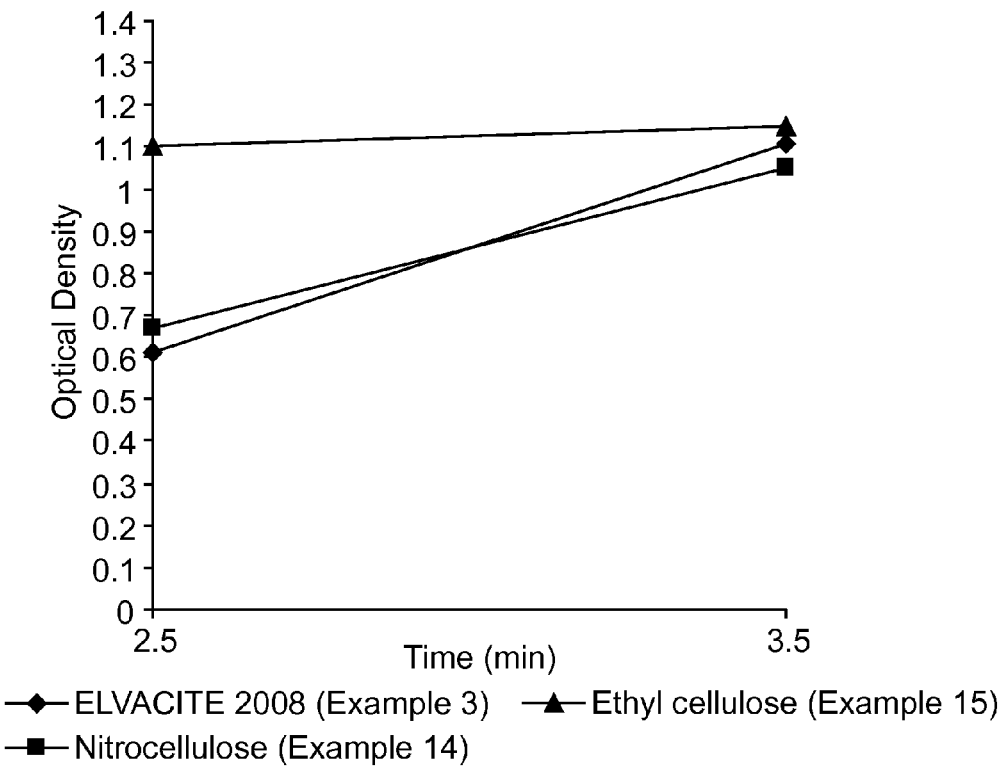
Figure 3:
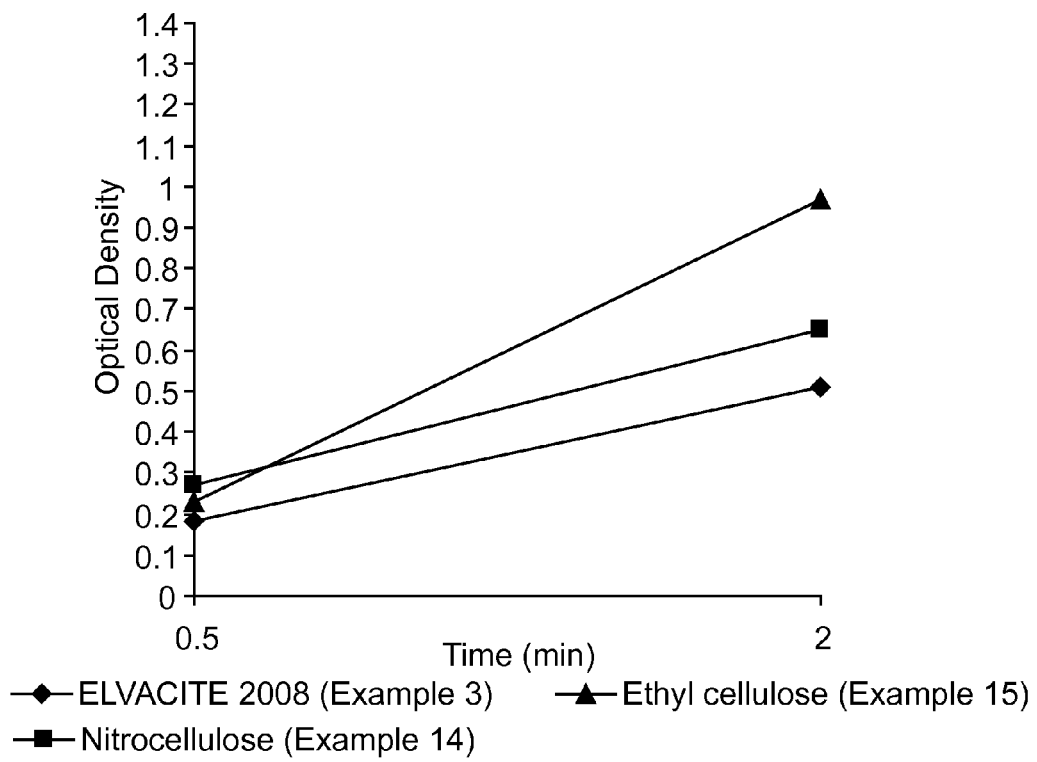
FIG. 3 is plots of optical density versus time for compositions described herein containing a binder with acid groups and a binder which produces an acid, compared with a neutral binder after exposure to steam at 134° C. for 0.5 and 2.0 minutes.

To the binder solution was added 21.28 g bismuth subsalicylate (Alfa Aesar, Ward Hill, Mass.), 64 g elemental sulfur (Akrochem, Akron, Ohio), and 85.2 g lithium carbonate (J. T. Baker, Phillipsburg, N.J.), and 0.19 g C.I. Pigment Yellow 12 (CAS No. 6358-85-6, Clariant Corp., Coventry, R.I.). The resulting mixture was milled using Zirstar zirconium oxide/yttrium oxide 1 mm beads (GEMCO, Atlanta, Ga.) in a Hockmeyer Micromill (Hockmeyer Equipment Corporation, Elizabeth City, N.C.) for 120 minutes. Samples were coated onto white index paper, grade 5515-138 (Monadnock Paper Mills, Bennington, N.H.) using a #22 Meyer Bar. The coated paper was dried at 50° C. for 5 minutes, cut into approximately 0.64 cm (0.25 inch) by 3.8 cm (1.5 inch) strips, and then exposed to steam in a Joslyn resistometer at 121° C., 132° C., and 134° C. for various time periods. The optical densities (OD) of the exposed samples were measured using a Macbeth RD917 densitometer using a white filter. Results of the experiment are reported in Table 3 and FIGS. 1, 2, and 3.

TABLE 3

| Bismuth subsalicylate/sulfur/lithium carbonate/ELVACITE 2008 | | | |
|---|---|---|---|
| Time (min) | 121° C. OD | 132° C. OD | 134° C. OD |
| 0.5 | — | — | 0.18 |
| 2 | — | — | 0.51 |
| 2.5 | — | 0.61 | — |
| 3 | 0.26 | — | — |
| 3.5 | — | — | 1.11 |
| 10 | 1.09 | — | — |

The results show optical densities greater than 0.4 for 134° C., 2 min and 121° C., 10 min cycles and a difference of greater than 0.3 OD between those values and samples exposed at 134° C., 30 sec. and 121° C., 3 min, respectively. With ELVACITE 2008, a reduced OD was found at 132° C. at 2.5 minutes and at 134° C. at 2 minutes compared to the OD found at these conditions with the formulation of Example 2 comprising ELVACITE 2013, which has a lower acid number than ELVACITE 2008.

Example 4

Bismuth Acetate with Poly(methyl methacrylate) Binder

A binder solution was prepared by mixing 100 g poly(methyl methacrylate) (ELVACITE 2008, acid number=9, available from Lucite International, Cordova, Tenn.) with 261.6 g n-propyl acetate and 175.4 g n-propyl alcohol. The mixture was rolled overnight in a jar to give a homogeneous solution.

To the binder solution was added 21.28 g bismuth acetate (Alfa Aesar, Ward Hill, Mass.), 64 g elemental sulfur (Akrochem, Akron, Ohio), and 85.2 g lithium carbonate (J. T. Baker, Phillipsburg, N.J.), and 0.19 g C.I. Pigment Yellow 12 (CAS No. 6358-85-6, Clariant Corp., Coventry, R.I.). The resulting mixture was milled using Zirstar zirconium oxide/yttrium oxide 1 mm beads (GEMCO, Atlanta, Ga.) in a Hockmeyer 1/16 basket mill (Hockmeyer Equipment Corporation, Elizabeth City, N.C.) for 90 minutes. The samples were coated onto white index paper, grade 5515-138 (Monadnock Paper Mills, Bennington, N.H.) using a #22 Meyer Bar. The coated papers were dried at 50° C. for 5 minutes, cut into approximately 0.64 cm (0.25 inch) by 3.8 cm (1.5 inch) strips, and then exposed to steam in a Joslyn resistometer at 121° C., 132° C., and 134° C. for various time periods. The optical densities (OD) of the exposed samples were measured using a Macbeth RD917 densitometer using a white filter. Results of the experiment are reported in Table 4 and FIG. 1.

TABLE 4

| Bismuth acetate/sulfur/lithium carbonate/ELVACITE 2008 | | | |
|---|---|---|---|
| Time (min) | 121° C. OD | 132° C. OD | 134° C. OD |
| 0.5 | — | — | 0.19 |
| 2 | — | — | 0.74 |
| 2.5 | — | 0.83 | — |
| 3 | 0.40 | — | — |
| 3.5 | — | — | 1.15 |
| 10 | 1.20 | — | — |

The results show optical densities greater than 0.4 for 134° C., 2 min and 121° C., 10 min cycles and a difference of greater than 0.3 OD between those values and samples exposed at 134° C., 30 sec. and 121° C., 3 min, respectively.

Example 5

Bismuth Citrate with Poly(methyl methacrylate) Binder

A binder solution was prepared by mixing 100 g poly (methyl methacrylate) (ELVACITE 2008, acid number=9, available from Lucite International, Cordova, Tenn.) with 261.6 g n-propyl acetate and 175.4 g n-propyl alcohol. The mixture was rolled overnight in a jar to give a homogeneous solution.

To the binder solution was added 21.28 g bismuth citrate (Alfa Aesar, Ward Hill, Mass.), 64 g elemental sulfur (Akrochem, Akron, Ohio), and 85.2 g lithium carbonate (J. T. Baker, Phillipsburg, N.J.), and 0.19 g C.I. Pigment Yellow 12 (CAS No. 6358-85-6, Clariant Corp., Coventry, R.I.). The resulting mixture was milled using Zirstar zirconium oxide/yttrium oxide 1 mm beads (GEMCO, Atlanta, Ga.) in a Hockmeyer 1/16 basket mill (Hockmeyer Equipment Corporation, Elizabeth City, N.C.) for 90 minutes. The samples were coated onto white index paper, grade 5515-138 (Monadnock Paper Mills, Bennington, N.H.) using a #22 Meyer Bar. The coated papers were dried at 50° C. for 5 minutes, cut into approximately 0.64 cm (0.25 inch) by 3.8 cm (1.5 inch) strips, and then exposed to steam in a Joslyn resistometer at 121° C., 132° C., and 134° C. for various time periods. The optical densities (OD) of the exposed samples were measured using a Macbeth RD917 densitometer using a white filter. Results of the experiment are reported in Table 5 and FIG. 1.

TABLE 5

| Bismuth citrate/sulfur/lithium carbonate/ELVACITE 2008 | | | |
|---|---|---|---|
| Time (min) | 121° C. OD | 132° C. OD | 134° C. OD |
| 0.5 | — | — | 0.13 |
| 2 | — | — | 0.41 |
| 2.5 | — | 0.60 | — |
| 3 | 0.34 | — | — |
| 3.5 | — | — | 1.15 |
| 10 | 1.24 | — | — |

The results show optical densities greater than 0.4 for 134° C., 2 min and 121° C., 10 min cycles and a difference of greater than 0.3 OD between the value at 121° C., 10 min and samples exposed at 121° C., 3 min.

Examples 7-9

Bismuth Subsalicylate with Poly(methyl methacrylate) Binder and Added Citric, Phthalic, p-Nitrobenzoic, or 2-Hydroxybenzoic Acid A binder solution was prepared by mixing 100 g poly (methyl methacrylate) (ELVACITE 2008, acid number=9, available from Lucite International, Cordova, Tenn.) with 261.6 g n-propyl acetate and 175.4 g n-propyl alcohol. The mixture was rolled overnight in a jar to give a homogeneous solution.

Figure 4:
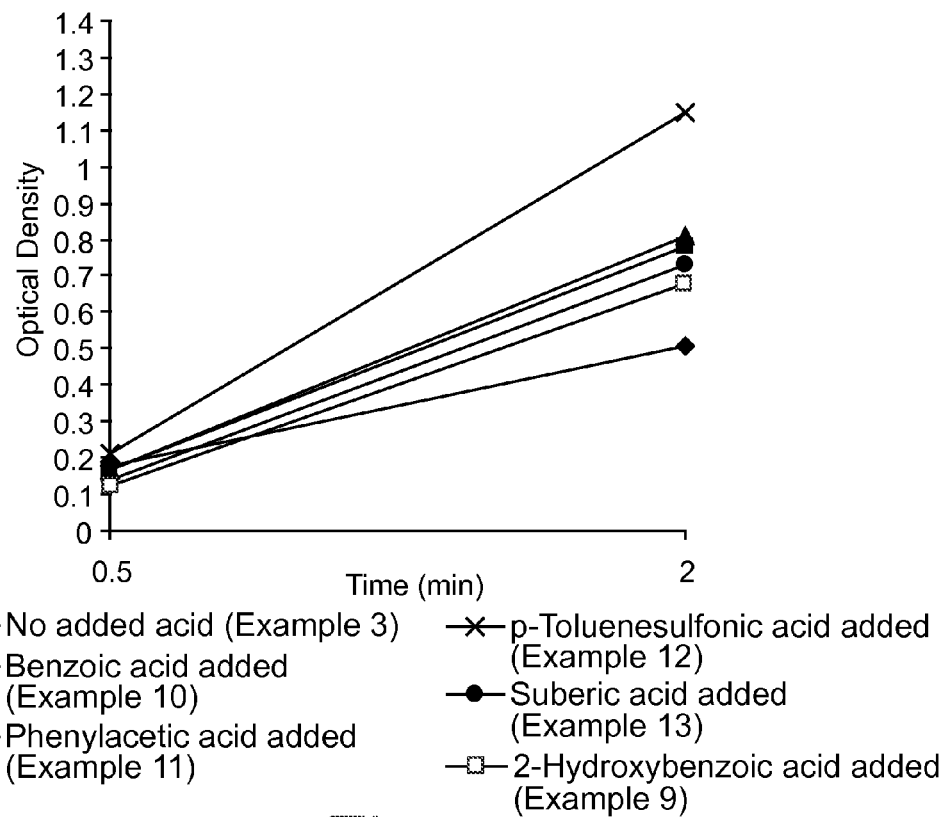
FIG. 4 is plots of optical density versus time for compositions described herein containing certain added acids compared with no added acid after exposure to steam at 134° C. for 0.5 and 2.0 minutes.

To the binder solution was added 21.28 g bismuth subsalicylate (Alfa Aesar, Ward Hill, Mass.), 64 g elemental sulfur (Akrochem, Akron, Ohio), 85.2 g lithium carbonate (J. T. Baker, Phillipsburg, N.J.), 0.19 g C.I. Pigment Yellow 12 (CAS No. 6358-85-6, Clariant Corp., Coventry, R.I.), and one of the following acids: 10 g phthalic acid, 10 g p-nitrobenzoic acid, or 10 g 2-hydroxybenzoic acid (all from Aldrich Chemical Corp., Milwaukee, Wis.). The resulting mixture was milled using Zirstar zirconium oxide/yttrium oxide 1 mm beads (GEMCO, Atlanta, Ga.) in a Hockmeyer 1/16 basket mill (Hockmeyer Equipment Corporation, Elizabeth City, N.C.) for 90 minutes. The sample was coated onto white index paper, grade 5515-138 (Monadnock Paper Mills, Bennington, N.H.) using a #22 Meyer Bar. The coated paper was dried at 50° C. for 5 minutes, cut into approximately 0.64 cm (0.25 inch) by 3.8 cm (1.5 inch) strips, and then exposed to steam in a Joslyn resistometer at 121° C., 132° C., and 134° C. for various time periods. The optical densities (OD) of the exposed samples were measured using a Macbeth RD917 densitometer using a white filter. Results of the experiment are reported in Table 6 and FIG. 4 (Example 9).

TABLE 6

| Bismuth subsalicylate/sulfur/lithium carbonate/ELVACITE 2008/acid | | | | |
|---|---|---|---|---|
| Temp., Time | Ex. 3 OD | Ex. 7 OD | Ex. 8 OD | Ex. 9 OD |
| 134° C., 3.5 min | 1.11 | 1.19 | 0.98 | 1.17 |
| 132° C., 2.5 min | 0.61 | 0.65 | 0.61 | 1.03 |
| 121° C., 10 min | 1.09 | 1.03 | 1.05 | 1.05 |
| 121° C., 3 min | 0.26 | 0.29 | 0.26 | 0.30 |
| 134° C., 2 min | 0.51 | 0.37 | 0.35 | 0.65 |
| 134° C., 30 sec | 0.18 | 0.15 | 0.14 | 0.13 |

Ex. 3 (Example 3) had no additional acid added.
Ex. 7 (Example 7) had phthalic acid added.
Ex. 8 (Example 8) had p-nitrobenzoic acid added.
Ex. 9 (Example 9) had 2-hydroxybenzoic acid added.

The added acids were found to affect the color change profiles of the chemical indicator compositions. For example, addition of 2-hydroxybenzoic acid was found to raise the OD of the composition of Example 8 when exposed to steam at 134° C. for 2 minutes compared with the composition of Example 3 with no added acid. In addition, a greater difference between the OD after 2 minutes at 134° C. and the OD at the fail cycle of 0.5 minutes at 134° C. was obtained. These results provide for an improved class 1 indicator.

Examples 10-13

Bismuth Subsalicylate with Poly(methyl methacrylate) Binder and Added Benzoic, Phenylacetic, p-Toluenesulfonic, or Suberic Acid A binder solution was prepared by mixing 100 g poly (methyl methacrylate) (ELVACITE 2008, acid number=9, available from Lucite International, Cordova, Tenn.) with 261.6 g n-propyl acetate and 175.4 g n-propyl alcohol. The mixture was rolled overnight in a jar to give a homogeneous solution.

To the binder solution were added 21.28 g bismuth subsalicylate (Alfa Aesar, Ward Hill, Mass.), 64 g elemental sulfur (Akrochem, Akron, Ohio), 85.2 g lithium carbonate (J. T. Baker, Phillipsburg, N.J.), 0.19 g C.I. Pigment Yellow 12 (CAS No. 6358-85-6, Clariant Corp., Coventry, R.I.), and 10 grams of benzoic acid, phenylacetic acid, p-toluenesulfonic acid, or suberic acid (all from Aldrich Chemical Corp., Milwaukee, Wis.). The resulting mixture was milled 120 minutes using Zirstar zirconium oxide/yttrium oxide 1 mm beads (GEMCO, Atlanta, Ga.) in a Hockmeyer Micromill (Hockmeyer Equipment Corporation, Elizabeth City, N.C.). Approximately 5 ml of sample was coated onto white index paper (grade 5515-138 (Monadnock Paper Mills, Bennington, N.H., pH=5.75). The samples were dried at 50° C. for 5 minutes, cut into approximately 0.64 cm (0.25 inch) by 3.8 cm (1.5 inch) strips, and then exposed to steam in an Joslyn resistometer at 121° C., 132° C., and 134° C. for various time periods. The optical densities (OD) of the exposed samples were measured using a Macbeth RD917 densitometer using a white filter. Results of the experiment are reported in the Table 7 and FIG. 4.

TABLE 7

Bismuth subsalicylate/sulfur/lithium carbonate/ELVACITE 2008/acid

| Temp., Time | Ex. 3 OD | Ex. 10 OD | Ex. 11 OD | Ex. 12 OD | Ex. 13 OD |
| --- | --- | --- | --- | --- | --- |
| 134° C., 3.5 min | 1.11 | 1.18 | 1.25 | 1.19 | 1.14 |
| 132° C., 2.5 min | 0.61 | 0.95 | 0.91 | 1.13 | 0.91 |
| 121° C., 10 min | 1.09 | 1.19 | 1.22 | 1.23 | 1.13 |
| 121° C., 3 min | 0.26 | 0.42 | 0.36 | 0.57 | 0.45 |
| 134° C., 2 min | 0.51 | 0.78 | 0.81 | 1.15 | 0.73 |
| 134° C., 30 sec | 0.18 | 0.17 | 0.17 | 0.21 | 0.14 |

Ex. 3 (Example 3) had no additional acid added.
Ex. 10 (Example 10) had benzoic acid added.
Ex. 11 (Example 11) had phenylacetic acid added.
Ex. 12 (Example 12) had p-toluenesulfonic acid added.
Ex. 13 (Example 13) had suberic acid added.

The addition of benzoic, phenylacetic, p-toluenesulfonic, or suberic acid was found to be advantageous when preparing a class 1 indicator in that the acids raise the OD after exposure for 2 minutes at 134° C. compared with the Example 3 with no added acid.

Examples 14-15

Bismuth Subsalicylate with Nitrocellulose and Ethyl Cellulose

A nitrocellulose binder solution was prepared by mixing 403.6 g nitrocellulose (code 6C1456, clear NC past, RD80883, Penn Color, Doylestown, Pa.) with 132.4 g of a 40/60 weight ratio of n-propyl alcohol/n-propyl acetate. The mixture was rolled overnight in a jar to give a homogeneous solution.

An ethyl cellulose binder solution was prepared by mixing 100 g ethyl cellulose (15% solids in toluene/ethanol 80/20 weight ratio, Ethocel Standard 7, lot UB01013T01, Dow Chemical, Midland, Mich.) and 436 g of a 40/60 weight ratio of n-propyl alcohol/n-propyl acetate. The mixture was rolled overnight in a jar to give a homogeneous solution.

To each of the binder solutions was added 21.28 g bismuth subsalicylate (Alfa Aesar, Ward Hill, Mass.), 64 g elemental sulfur (Akrochem, Akron, Ohio), 85.2 g lithium carbonate (J. T. Baker, Phillipsburg, N.J.), and 0.19 g C.I. Pigment Yellow 12 (CAS No. 6358-85-6, Clariant Corp., Coventry, R.I.). The resulting mixtures were milled using Zirstar zirconium oxide/yttrium oxide 1 mm beads (GEMCO, Atlanta, Ga.) in a Hockmeyer 1/16 basket mill (Hockmeyer Equipment Corporation, Elizabeth City, N.C.) for 90 minutes. A few ml of each sample were coated separately onto white index paper (grade 5515-138 (Monadnock Paper Mills, Bennington, N.H., pH=5.75) using a #22 Meyer Bar. The samples were dried at 50° C. for 5 minutes, cut into approximately 0.64 cm (0.25 inch) by 3.8 cm (1.5 inch) strips, and then exposed to steam in a Joslyn resistometer at 121° C., 132° C., and 134° C. for various time periods. The optical densities (OD) of the exposed samples were measured using a Macbeth RD917 densitometer using a white filter. Results of the experiments are reported in Table 8 and FIGS. 2 and 3.

TABLE 8

Bismuth subsalicylate/sulfur/lithium carbonate/nitrocellulose, ethyl cellulose, ELVACITE 2008, or ELVACITE 2013

| Temp., Time | Ex. 3 OD | Ex. 14 OD | Ex. 15 OD |
| --- | --- | --- | --- |
| 134° C., 3.5 min | 1.11 | 1.05 | 1.15 |
| 132° C., 2.5 min | 0.61 | 0.67 | 1.1 |
| 121° C., 10 min | 1.09 | 0.9 | 1.12 |
| 121° C., 3 min | 0.26 | 0.52 | 0.66 |
| 134° C., 2 min | 0.51 | 0.65 | 0.97 |
| 134° C., 30 sec | 0.18 | 0.27 | 0.23 |

Ex. 3 (Example 3) had ELVACITE 2008 as a binder
Ex. 14 (Example 14) had nitrocellulose as a binder.
Ex. 15 (Example 15) had ethyl cellulose as a binder.

Binders with different acidities were found to effect color change of the chemical indicator compositions. For a class 4 indicator with stated value pass of 134° C., 3.5 min and fail of 132° C., 2 min 37 sec, the nitrocellulose and ELVACITE 2008 resin were found to be good choices for a binder since compositions containing these binders give larger changes in OD on exposure to these steam conditions compared with the neutral ethyl cellulose. On the other hand, for a class 1 indicator, ethyl cellulose was found to be a good choice for a binder since compositions containing this binder give larger changes in optical density on exposure to steam at 134° C. for 2 min compared with those using nitrocellulose and ELVACITE 2008.

Examples 16-18

Bismuth Subsalicylate with Poly(methyl methacrylate) on Various pH Paper Substrates A binder solution was prepared by mixing 100 g poly (methyl methacrylate) (ELVACITE 2008, acid number=9, available from Lucite International, Cordova, Tenn.) with 261.6 g n-propyl acetate and 175.4 g n-propyl alcohol. The mixture was rolled overnight in a jar to give a homogeneous solution.

To the binder solution was added 21.28 g bismuth subsalicylate (Alfa Aesar, Ward Hill, Mass.), 64 g elemental sulfur (Akrochem, Akron, Ohio), 85.2 g lithium carbonate (J. T. Baker, Phillipsburg, N.J.), and 0.19 g C.I. Pigment Yellow 12 (CAS No. 6358-85-6, Clariant Corp., Coventry, R.I.). The resulting mixture was milled using Zirstar zirconium oxide/yttrium oxide 1 mm beads (GEMCO, Atlanta, Ga.) in a Hockmeyer Micromill (Hockmeyer Equipment Corporation, Elizabeth City, N.C.) for 120 minutes. Approximately 5 ml of sample was coated onto white index paper, grade 5515-138 (Monadnock Paper Mills, Bennington, N.H., pH=5.75) and the following papers from Wausau (Mosinee, Wis.): grade 5170, 1385 white, pH=8.0; grade 3245, 1385 white, pH=7.2; grade 3383, 1214 white, pH=6.8, using a #22 Meyer Bar. The samples were dried at 50° C. for 5 minutes, cut into approximately 0.64 cm (0.25 inch) by 3.8 cm (1.5 inch) strips, and then exposed to steam in a Joslyn resistometer at 121° C., 132° C., and 134° C. for various time periods. The optical densities (OD) of the exposed samples were measured using a Macbeth RD917 densitometer using a white filter. Results of the experiments are reported in Table 9 and FIGS. 5 and 6.

TABLE 9

Bismuth subsalicylate/sulfur/lithium carbonate/ELVACITE 2008 on pH 5.7, 6.8, 7.2, and 8.0 Papers

| Temp., Time | Ex. 3 OD | Ex. 16 OD | Ex. 17 OD | Ex. 18 OD |
|---|---|---|---|---|
| 134° C., 3.5 min | 1.11 | 1.09 | 1.13 | 1.14 |
| 132° C., 2.5 min | 0.61 | 1.05 | 0.98 | 1.05 |
| 121° C., 10 min | 1.09 | 1.17 | 1.19 | 1.15 |
| 121° C., 3 min | 0.26 | 0.54 | 0.65 | 0.63 |
| 134° C., 2 min | 0.51 | 1.01 | 0.92 | 1.00 |
| 134° C., 30 sec | 0.18 | 0.21 | 0.19 | 0.21 |

Ex. 3 (Example 3) had the composition coated on pH 5.75 paper.
Ex. 16 (Example 16) had the composition coated on pH 6.8 paper.
Ex. 17 (Example 17) had the composition coated on pH 7.2 paper.
Ex. 18 (Example 18) had the composition coated on pH 8 paper.

The pH of the paper onto which the composition was coated was found to affect the color change characteristics of the composition. For a class 4 indicator with stated value pass of 134° C., 3.5 min and fail of 132° C., 2 min 37 sec, the pH 5.75 paper was found to be a good choice for a substrate since compositions coated on this substrate give a larger change in OD between these steam conditions compared with the papers having a higher pH. On the other hand, for a class 1 indicator, papers with a pH of 6.8, 7.2, and 8 were found to be good choices for a substrate since compositions coated on these substrates gave larger changes in optical density on exposure to steam at 134° C. for 2 min compared with those coated on the pH 5.75 paper.

Example 19

Bismuth Neodecanoate with Poly(methyl methacrylate)

A binder solution was prepared by mixing 100 g poly (methyl methacrylate) (ELVACITE 2008, acid number=9, available from Lucite International, Cordova, Tenn.) with 261.6 g n-propyl acetate and 175.4 g n-propyl alcohol. The mixture was rolled overnight in a jar to give a homogeneous solution.

To the binder solution was added 21.28 g bismuth neodecanoate (Aldrich, Milwaukee, Wis.), 64 g elemental sulfur (Akrochem, Akron, Ohio), and 85.2 g lithium carbonate (J. T. Baker, Phillipsburg, N.J.)), and 0.19 g C.I. Pigment Yellow 12 (CAS No. 6358-85-6, Clariant Corp., Coventry, R.I.). The resulting mixture was milled using Zirstar zirconium oxide/yttrium oxide 1 mm beads (GEMCO, Atlanta, Ga.) in a Hockmeyer Micromill (Hockmeyer Equipment Corporation, Elizabeth City, N.C.) for 120 minutes. Approximately 5 ml of sample was coated onto white index paper, grade 5515-138 (Monadnock Paper Mills, Bennington, N.H.) using a #22 Meyer Bar. The coated paper was dried at 50° C. for 5 minutes, cut into approximately 0.64 cm (0.25 inch) by 3.8 cm (1.5 inch) strips, and then exposed to steam in a Joslyn resistometer at 121° C., 132° C., and 134° C. for various time periods. The optical densities of the exposed samples were measured using a Macbeth RD917 densitometer using a white filter. Results of the experiment are reported in Table 10 and FIG. 1.

TABLE 10

Bismuth neodecanoate/sulfur/lithium carbonate/ELVACITE 2008

| Temp., Time | Optical Density |
|---|---|
| 134° C., 3.5 min | 1.03 |
| 132° C., 2.5 min | 0.75 |
| 121° C., 10 min | 1.16 |
| 121° C., 3 min | 0.41 |
| 134° C., 2 min | 0.65 |
| 134° C., 30 sec | 0.25 |

The results show optical densities greater than 0.4 for 134° C., 2 min and 121° C., 10 min cycles and a difference of greater than 0.3 OD between those values and samples exposed at 134° C., 30 sec. and 121° C., 3 min, respectively.

Example 20

Bismuth (III) Oxide with Poly(methyl methacrylate)

A binder solution was prepared by mixing 100 g poly (methyl methacrylate) (ELVACITE 2008, acid number=9, available from Lucite International, Cordova, Tenn.) with 261.6 g n-propyl acetate and 175.4 g n-propyl alcohol. The mixture was rolled overnight in a jar to give a homogeneous solution.

To the binder solution was added 21.28 g bismuth (III) oxide (Aldrich, Milwaukee, Wis.), 64 g elemental sulfur (Akrochem, Akron, Ohio), and 85.2 g lithium carbonate (J. T. Baker, Phillipsburg, N.J.)), and 0.19 g C.I. Pigment Yellow 12 (CAS No. 6358-85-6, Clariant Corp., Coventry, R.I.). The resulting mixture was milled using Zirstar zirconium oxide/yttrium oxide 1 mm beads (GEMCO, Atlanta, Ga.) in a Hockmeyer Micromill (Hockmeyer Equipment Corporation, Elizabeth City, N.C.) for 120 minutes. Approximately 5 ml of sample was coated onto white index paper, grade 5515-138, pH 5.75 (Monadnock Paper Mills, Bennington, N.H.) using a #22 Meyer Bar. The coated papers were dried at 50° C. for 5 minutes, cut into approximately 0.64 cm (0.25 inch) by 3.8 cm (1.5 inch) strips, and then exposed to steam in a Joslyn resistometer at 121° C., 132° C., and 134° C. for various time periods. The optical densities of the exposed samples were measured using a Macbeth RD917 densitometer using a white filter. Results of the experiment are reported in Table 11 and FIG. 1.

TABLE 11

Bismuth (III) oxide/sulfur/lithium carbonate/ELVACITE 2008

| Temp., Time | Optical Density |
|---|---|
| 134° C., 3.5 min | 0.92 |
| 132° C., 2.5 min | 0.85 |
| 121° C., 10 min | 1.05 |
| 121° C., 3 min | 0.54 |
| 134° C., 2 min | 0.78 |
| 134° C., 30 sec | 0.32 |

The results show optical densities greater than 0.4 for 134° C., 2 min and 121° C., 10 min cycles and a difference of greater than 0.3 OD between those values and samples exposed at 134° C., 30 sec. and 121° C., 3 min, respectively.

Example 21

Bismuth Subcarbonate with Poly(methyl methacrylate)

A binder solution was prepared by mixing 100 g poly (methyl methacrylate) (ELVACITE 2008, acid number=9, available from Lucite International, Cordova, Tenn.) with 261.6 g n-propyl acetate and 175.4 g n-propyl alcohol. The mixture was rolled overnight in a jar to give a homogeneous solution.

To the binder solution was added 21.28 g bismuth subcarbonate (Dudley Chemical Corp., Lakewood, N.J.), 64 g elemental sulfur (Akrochem, Akron, Ohio), and 85.2 g lithium carbonate (J. T. Baker, Phillipsburg, N.J.), and 0.19 g C.I. Pigment Yellow 12 (CAS No. 6358-85-6, Clariant Corp., Coventry, R.I.). The resulting mixture was milled using Zirstar zirconium oxide/yttrium oxide 1 mm beads (GEMCO, Atlanta, Ga.) in a Hockmeyer Micromill (Hockmeyer Equipment Corporation, Elizabeth City, N.C.) for 120 minutes. Approximately 5 ml of sample was coated onto white index paper, grade 5515-138 (Monadnock Paper Mills, Bennington, N.H.) using a #22 Meyer Bar. The coated paper was dried at 50° C. for 5 minutes, cut into approximately 0.64 cm (0.25 inch) by 3.8 cm (1.5 inch) strips, and then exposed to steam in a Joslyn resistometer at 121° C., 132° C., and 134° C. for various time periods. The optical densities of the exposed samples were measured using a Macbeth RD917 densitometer using a white filter. Results of the experiment are reported in Table 12 and FIG. 1.

TABLE 12

Bismuth subcarbonate/sulfur/lithium carbonate/ELVACITE 2008

| Temp., Time | Optical Density |
|---|---|
| 134° C., 3.5 min | 0.70 |
| 132° C., 2.5 min | 0.46 |
| 121° C., 10 min | 0.77 |
| 121° C., 3 min | 0.26 |
| 134° C., 2 min | 0.48 |
| 134° C., 30 sec | 0.18 |

The results show optical densities greater than 0.4 for 134° C., 2 min and 121° C., 10 min cycles and a difference of greater than 0.3 OD between those values and samples exposed at 134° C., 30 sec. and 121° C., 3 min, respectively.

Example 22

Bismuth Diethyldithiocarbamate with Poly(methyl methacrylate)

A binder solution was prepared by mixing 100 g poly (methyl methacrylate) (ELVACITE 2008, acid number=9, available from Lucite International, Cordova, Tenn.) with 261.6 g n-propyl acetate and 175.4 g n-propyl alcohol. The mixture was rolled overnight in a jar to give a homogeneous solution.

To the binder solution was added 21.28 g bismuth diethyldithiocarbamate (Shepherd Chemical Company, Cincinnati, Ohio), 64 g elemental sulfur (Akrochem, Akron, Ohio), and 85.2 g lithium carbonate (J. T. Baker, Phillipsburg, N.J.), and 0.19 g C.I. Pigment Yellow 12 (CAS No. 6358-85-6, Clariant Corp., Coventry, R.I.). The resulting mixture was milled using Zirstar zirconium oxide/yttrium oxide 1 mm beads (GEMCO, Atlanta, Ga.) in a Hockmeyer Micromill (Hockmeyer Equipment Corporation, Elizabeth City, N.C.) for 120 minutes. Approximately 5 ml of sample was coated onto white index paper, grade 5515-138 (Monadnock Paper Mills, Bennington, N.H.) using a #22 Meyer Bar. The coated paper was dried at 50° C. for 5 minutes, cut into approximately 0.64 cm (0.25 inch) by 3.8 cm (1.5 inch) strips, and then exposed to steam in a Joslyn resistometer at 121° C., 132° C., and 134° C. for various time periods. The optical densities of the exposed samples were measured using a Macbeth RD917 densitometer using a white filter. Results of the experiment are reported in Table 13 and FIG. 1.

TABLE 13

Bismuth diethyldithiocarbamate/sulfur/lithium carbonate/ELVACITE 2008

| Temp., Time | Optical density |
|---|---|
| 134° C., 3.5 min | 0.67 |
| 132° C., 2.5 min | 0.44 |
| 121° C., 10 min | 0.87 |
| 121° C., 3 min | 0.26 |
| 134° C., 2 min | 0.39 |
| 134° C., 30 sec | 0.17 |

The results indicate that bismuth diethyldithiocarbamate in ELVACITE 2008 resin undergoes a color change when exposed to steam.

Example 23

Bismuth Subcarbonate/Sulfur/Lithium Carbonate at Different Ratios than Example 21 with Poly(methyl methacrylate)

A binder solution was prepared by mixing 100 g poly (methylmethacrylate) (ELVACITE 2008, acid number=9, available from Lucite International, Cordova, Tenn.) with 261.6 g n-propyl acetate and 175.4 g n-propyl alcohol. The mixture was rolled overnight in a jar to give a homogeneous solution.

To the binder solution was added 74.12 g bismuth subcarbonate (Dudley Chemical Corp., Lakewood, N.J.), 74.12 g elemental sulfur (Akrochem, Akron, Ohio), 22.24 g lithium carbonate (J. T. Baker, Phillipsburg, N.J.), and 0.19 g C.I. Pigment Yellow 12 (CAS No. 6358-85-6, Clariant Corp., Coventry, R.I.). The resulting mixture was milled using Zirstar zirconium oxide/yttrium oxide 1 mm beads (GEMCO, Atlanta, Ga.) in a Hockmeyer Micromill (Hockmeyer Equipment Corporation, Elizabeth City, N.C.) for 120 minutes. Approximately 5 ml of sample was coated onto white index paper, grade 5515-138 (Monadnock Paper Mills, Bennington, N.H.) using a #22 Meyer Bar. The coated paper was dried at 50° C. for 5 minutes, cut into approximately 0.64 cm (0.25 inch) by 3.8 cm (1.5 inch) strips, and then exposed to steam in a Joslyn resistometer at 121° C., 132° C., and 134° C. for various time periods. The optical densities of the exposed samples were measured using a Macbeth RD917 densitometer using a white filter. Results of the experiment are reported in Table 14 and FIG. 1.

TABLE 14

Bismuth subcarbonate/sulfur/lithium carbonate/ELVACITE 2008

| Temp., Time | Optical Density |
|---|---|
| 134° C., 3.5 min | 0.80 |
| 132° C., 2.5 min | 0.60 |
| 121° C., 10 min | 0.84 |
| 121° C., 3 min | 0.32 |
| 134° C., 2 min | 0.59 |
| 134° C., 30 sec | 0.21 |

Example 24

Bismuth Subgallate with Poly(methyl methacrylate) Binder

A binder solution was prepared by mixing 100 g poly (methyl methacrylate) (ELVACITE 2008, acid number=9, available from Lucite International, Cordova, Tenn.) with 261.6 g n-propyl acetate and 175.4 g n-propyl alcohol. The mixture was rolled overnight in a jar to give a homogeneous solution.

To the binder solution was added 21.28 g bismuth subgallate (Alfa Aesar, Ward Hill, Mass.), 64 g elemental sulfur (Akrochem, Akron, Ohio), and 85.2 g lithium carbonate (J. T. Baker, Phillipsburg, N.J.), and 0.19 g C.I. Pigment Yellow 12 (CAS No. 6358-85-6, Clariant Corp., Coventry, R.I.). The resulting mixture was milled using Zirstar zirconium oxide/yttrium oxide 1 mm beads (GEMCO, Atlanta, Ga.) in a Hockmeyer Micromill (Hockmeyer Equipment Corporation, Elizabeth City, N.C.) for 120 minutes. Samples were coated onto white index paper, grade 5515-138 (Monadnock Paper Mills, Bennington, N.H.) using a #22 Meyer Bar. The coated paper was dried at 50° C. for 5 minutes, cut into approximately 0.64 cm (0.25 inch) by 3.8 cm (1.5 inch) strips, and then exposed to steam in a Joslyn resistometer at 121° C., 132° C., and 134° C. for various time periods. The optical densities (OD) of the exposed samples were measured using a Macbeth RD917 densitometer using a white filter. Results of the experiment are reported in Table 15 and FIG. 1.

TABLE 15

Bismuth subgallate/sulfur/lithium carbonate/ELVACITE 2008

| Time (min) | 121° C. OD | 132° C. OD | 134° C. OD |
|---|---|---|---|
| 0.5 | — | — | 0.17 |
| 2 | — | — | 0.32 |
| 2.5 | — | 0.48 | — |
| 3 | 0.28 | — | — |
| 3.5 | — | — | 0.80 |
| 10 | 1.14 | — | — |

The results show optical densities greater than 0.4 for the 121° C., 10 min cycle and a difference of greater than 0.3 OD between this value and samples exposed at 121° C., 3 min.

Example 25

Varnish I was prepared by mixing 40 parts acrylic resin (Acryloid DM-55 acrylic resin available from Rohm & Haas Co., Philadelphia, Pa.) and 60 parts glycol ether (Propasol M available from Ashland Specialty Chemical Company, Columbus, Ohio) in a glass jar on a roller mill until a homogeneous composition was formed.

Varnish II was prepared by mixing 30 parts ethyl cellulose (Aqualon 14 available from Hercules Inc., Hopewell, Va.) with 70 parts glycol ether in a glass jar on a roller mill until a homogeneous composition was formed.

Varnish III was prepared by mixing about 70 parts modified rosin resinate (Resinall 153 available from Resinall Corporation, Stamford, Conn.) with about 30 parts xylene in a glass jar on a roller mill until a homogeneous composition was formed.

A yellow tinting paste was prepared by mixing 44.5 parts yellow pigment (11-1003 DHG from Clariant Corp. of Coventry, R.I.), 18.3 parts glycol ether (Propasol M), and 37.2 parts Varnish I in a jar on a roller mill with grinding media until a homogeneous paste was formed.

A binder mixture was prepared by milling together the following materials until a homogeneous mixture was formed: 2.75 parts oxazoline surfactant (ALKATERGE™T oxazoline available from Angus Chemical Company, Buffalo Grove, Ill.), 24.54 parts glycol ether (Propasol M), 0.65 parts silica (BENTONE 14 available from Elementis Specialties, Inc., Hightstown, N.J.), 1.32 parts acetone, 16.96 parts Varnish I, 11.07 parts bismuth subsalicylate (Alfa Aesar, Ward Hill, Mass.), 17.71 parts elemental sulfur (Akrochem, Akron, Ohio), 21.23 parts lithium carbonate (J. T. Baker, Phillipsburg, N.J.), 1.27 part aluminum chloride hexahydrate (J. T. Baker, Phillipsburg, N.J.), and 2.50 parts Varnish II.

An ink composition was prepared by mixing the following materials in a ball mill on a roller mill to form a homogeneous mixture: 79.84 parts binder mixture, 7.40 parts Varnish I, 8.93 parts Varnish II, 3.53 parts glycol ether, and 0.30 part yellow tinting paste.

The ink composition was flexographically printed on a white sheet of paper (40 lb. Sterilizable Kraft Paper available from Monadnock Paper Mill, Bennington, N.H.) to a coating weight of about 0.1 grams of ink per sheet in the pattern shown on chemical indicator 1120 in FIG. 11. The ink was dried in an oven set at about 93° C.

A test pack assembly was prepared by stacking sheets measuring 12.6 cm by 11.05 cm as follows:
  sheet of blotter paper with polyester laminate on both sides
  foam pad
  8 blotter sheets (5610-227 paper available from Monadnock Paper Mills, Bennington, N.H.)
  indicator sheet—printed side facing the foam pad
  12 blotter sheets (5610-227 paper)
  sheet of blotter paper with polyester laminate on both sides The stack was then overwrapped with a central supply room overwrap (CSR Wrap 12127 available from Dexter Nonwovens from Windsor Locks, Conn.), and held shut with a test pack label.

The test packs were tested in two separate cycles, each having a fault condition in a standard sterilizer cycle. A third cycle was conducted with no fault conditions. For each cycle, two test packs made as described above and two comparative packs (commercially available test packs, Product No. 00135, available from 3M Company, St. Paul, Minn.) were placed in a steam sterilizer (AMSCO 3013) with an exposure time of 3.5 minutes. The indicator sheets from the comparative packs had been printed with a lead based ink with the print pattern shown, for example, in FIG. 9. In the first and second cycles, fault conditions were created using an air leak of 13.2 mm Hg change per minute into the sterilizer (as assessed with Air Leak Test Condition I). The third cycle was run with no air leak.

The test packs were cooled to room temperature and the indicator sheets were removed from the test packs and examined visually. All of the indicator sheets from the third cycle appeared uniformly black. All of the Example 25 sheets from the first and second cycles exhibited an area, having a somewhat circular shape with dimensions of 2.5 cm by 3 cm in one case and 3.2 cm by 3.5 cm in the other case and located toward the middle of the sheet, that had not turned black and that was distinctly lighter than the surrounding area. This was an indication of an air leak in the sterilizer. The comparative sheets for these cycles had very faint lighter areas that were less detectable to the eye, and although not distinct, their dimensions were approximately 1 cm by 1.2 cm in one case and 0.7 cm by 1 cm in the other case.

The optical density was measured in five spots across the sheets with a densitometer (MacBeth RD917). Each spot covered about a 3.18 mm diameter and care was taken to position the densitometer window completely over a printed area. The spots were selected as shown on the printed area in FIGS. 10a and 12: on each edge of the sheet, represented by edge spot 1055a in FIGS. 10a and 1255 in FIG. 12, in the middle of the air pocket, represented by central spot 1015a in FIGS. 10a and 1215 in FIG. 12, and on outer opposing edges of the air pocket, represented by peripheral spot 1035a in FIGS. 10a and 1235 in FIG. 12. The densitometer readings are shown in Table 12.

Optical density measurements were also taken at the corresponding spots of the Example 25 and comparative indicator sheets exposed to the third cycle with no air leak. The densitometer readings are shown in Table 12. All of these sheets were uniformly dark, with no indication of a lighter area. FIGS. 9 and 11 illustrate the appearance of these sheets from the comparative and Example 25 test packs, respectively.

TABLE 12

Optical Density Measurements on Bowie-Dick Indicator Sheets of FIGS. 10a and 12 with Air Pocket and FIGS. 9 and 11 without Air Pocket

| Indicator Sheet | Cycle | Optical Density | | | | | Greatest Differential |
|---|---|---|---|---|---|---|---|
| | | E1 | P1 | C | P2 | E2 | |
| Ex 25 - sheet 1 FIG. 10a | 1 | 1.26 | 0.92 | 0.88 | 0.90 | 1.28 | 0.38 |
| Ex 25 - sheet 2 FIG. 10a | 1 | 1.25 | 1.09 | 0.87 | 0.86 | 1.27 | 0.41 |
| Comparative - sheet 1 FIG. 12 | 1 | 1.02 | 0.93 | 0.91 | 0.97 | 1.04 | 0.13 |
| Comparative - sheet 2 FIG. 12 | 1 | 1.03 | 0.95 | 0.92 | 0.97 | 1.02 | 0.11 |
| Ex 25 - sheet 1 FIG. 10a | 2 | 1.25 | 0.96 | 0.87 | 0.92 | 1.28 | 0.41 |
| Ex 25 - sheet 2 FIG. 10a | 2 | 1.26 | 1.02 | 0.91 | 0.99 | 1.29 | 0.37 |
| Comparative - sheet 1 FIG. 12 | 2 | 1.04 | 0.98 | 0.92 | 0.95 | 1.03 | 0.12 |
| Comparative - sheet 2 FIG. 12 | 2 | 1.03 | 0.97 | 0.93 | 0.96 | 1.05 | 0.12 |
| Ex 25 - sheet 1 FIG. 11 | 3 | 1.25 | 1.25 | 1.23 | 1.26 | 1.28 | 0.03 |
| Ex 25 - sheet 2 FIG. 11 | 3 | 1.26 | 1.26 | 1.24 | 1.25 | 1.29 | 0.05 |
| Comparative - sheet 1 FIG. 9 | 3 | 1.04 | 1.03 | 1.02 | 1.02 | 1.03 | 0.02 |
| Comparative - sheet 2 FIG. 9 | 3 | 1.03 | 1.02 | 1.01 | 1.03 | 1.05 | 0.04 |

E1 = edge spot (1055a in FIG. 10a and 1255 in FIG. 12).
E2 = edge spot at corresponding location at opposite edge of the printed area of indicator sheet.
C = central spot (1015a in FIG. 10a and 1215 in FIG. 12).
P1 = peripheral spot (1035a in FIG. 10a and 1235 in FIG. 12).
P2 = peripheral spot on opposite side of central spot from P1.

The data in Table 12 show that the difference in optical density between edge of the sheet and center of the air pocket and between edge of the sheet and periphery of the air pocket was greater using the compositions of the invention. The difference was more apparent in the sheets of the invention to the unaided eye, so that a fault condition in the sterilizer can be more easily determined.

Example 26

Test packs were prepared as described in Example 25 except that in this case the print pattern of Product No. 00135 (3M Company, St. Paul, Minn.), illustrated, for example, in FIG. 9, was used on all sheets. The test packs as well as comparative packs (commercially available test packs, Product No. 00135, available from 3M Company, St. Paul, Minn.) were subjected to the same steam sterilizer cycle as the first cycle in Example 25, except that the measured air leak rate per Air Leak Test Condition I was 10 mm Hg per minute (cycle 4). The Example 26 indicator sheets exhibited a prominently visible area of lighter color as was found with the sheets of Example 25. The lighter areas had a somewhat circular shape with dimensions of 3 cm by 3.5 cm in one case and 3 cm by 5 cm in the other case. The comparative sheets with lead-based ink from Product No. 00135 test packs exhibited only very faintly lighter areas that were less detectable to the eye, and although not distinct, their dimensions were approximately 1 cm by 1.5 cm. A comparative test pack was also subjected to a cycle with no air leak (cycle 5), and the indicator sheet taken from the test pack was nearly uniformly darkened in appearance. FIG. 9 illustrates the appearance of this sheet.

Optical densities were measured as in Example 25. The spots were selected as shown on the printed area in FIGS. 10 and 12: on each edge of the sheet, represented by edge spot 1055 in FIGS. 10 and 1255 in FIG. 12, in the middle of the air pocket, represented by central spot 1015 in FIGS. 10 and 1215 in FIG. 12, and on outer opposing edges of the air pocket, represented by peripheral spot 1035 in FIGS. 10 and 1235 in FIG. 12. The densitometer readings are shown in Table 13.

Optical density measurements were also taken at the corresponding spots of the comparative indicator sheet (illustrated in FIG. 9) exposed to the cycle with no air leak (cycle 5). Results are shown in Table 13.

It is noted that the optical densities measured at the edge spots, representative of complete darkening from full steam exposure, of the comparative sheets were higher in Table 13 than in Table 12 as a result of lot-to-lot variations.

TABLE 13

Optical Density Measurements on Bowie-Dick Indicator Sheets of FIGS. 10 and 12 with Air Pocket and FIG. 9 without Air Pocket

| Indicator Sheet | Cycle | Optical Density | | | | | Greatest Differential |
|---|---|---|---|---|---|---|---|
| | | E1 | P1 | C | P2 | E2 | |
| Ex 26 - sheet 1 FIG. 10 | 4 | 1.20 | 0.75 | 0.70 | 0.86 | 1.19 | 0.50 |
| Ex 26 - sheet 2 FIG. 10 | 4 | 1.22 | 0.78 | 0.71 | 0.87 | 1.22 | 0.51 |
| Comparative - sheet 1 FIG. 12 | 4 | 1.19 | 1.09 | 1.04 | 1.10 | 1.19 | 0.15 |
| Comparative - sheet 2 FIG. 12 | 4 | 1.22 | 1.09 | 0.94 | 1.06 | 1.22 | 0.18 |
| Comparative sheet FIG. 9 | 5 | 1.21 | 1.20 | 1.18 | 1.19 | 1.20 | 0.03 |

E1 = edge spot (1055 in FIG. 10 and 1255 in FIG. 12).
E2 = edge spot at corresponding location at opposite edge of the printed area of indicator sheet.
C = central spot (1015 in FIG. 10 and 1215 in FIG. 12).
P1 = peripheral spot (1035 in FIG. 10 and 1235 in FIG. 12).
P2 = peripheral spot on opposite side of central spot from P1.

All references and publications or portions thereof cited herein are expressly incorporated herein by reference in their entirety into this disclosure. Exemplary embodiments of this invention are discussed and reference has been made to some possible variations within the scope of this invention. These and other variations and modifications in the invention will be apparent to those skilled in the art without departing from the scope of the invention, and it should be understood that this invention is not limited to the exemplary embodiments set forth herein. Accordingly, the invention is to be limited only by the embodiments provided below and equivalents thereof.

What is claimed is:

1. A chemical indicator composition comprising:
   a) a bismuth (III) compound comprising at least one organic group which includes 2 to 20 carbon atoms;
   b) elemental sulfur;
   c) a compound which makes the composition alkaline when exposed to water vapor at an elevated temperature; and
   d) an acid selected from the group consisting of 2-hydroxybenzoic acid, benzoic acid, p-toluenesulfonic acid, phenylacetic acid, citric acid, phthalic acid, suberic acid, and combinations thereof, wherein the acid is present in an amount of at least 0.005 equivalents acid per equivalent of the compound which makes the composition alkaline.

2. The composition of claim 1, wherein the bismuth (III) compound is selected from the group consisting of bismuth subsalicylate, bismuth gallate, bismuth subgallate, bismuth pyrogallate, bismuth acetate, bismuth citrate, bismuth potassium citrate, ammonium bismuth citrate, bismuth lactate, bismuth oxalate, bismuth benzoate, bismuth formate, bismuth propionate, bismuth butyrate, bismuth pivalate, 2-propylpentanoic acid bismuth salt, bismuth ascorbate, bismuth diethyldithiocarbamate, bismuth dimethyldithiocarbamate, bismuth 2-ethylhexanoate, bismuth neodecanoate, bismuth oleate, bismuth gluconate, bismuth potassium D-gluconate, bismuth naphtholate, naphthenic acid bismuth salt, bismuth triglycollamate, bismuth sodium triglycollamate, bismuth succinate, bismuth maleate, bismuth tartrate, bismuth sodium tartrate, bismuth potassium tartrate, bismuth tannate, 3-camphocarboxylic acid bismuth salt, bismuth ethylcamphorate, bismuth oxyquinoline, 2-oxo-3-bornanecarboxylic acid bismuth salt, bismuth valproate, and a combination thereof.

3. The composition of claim 1, wherein the compound which makes the composition alkaline has a solubility in water at 100° C. of not more than 1 gram per 100 cubic centimeters of water.

4. The composition of claim 1, wherein the bismuth (III) compound and the elemental sulfur are present in a weight ratio of not more than 2:3 and not less than 0.5:3; and wherein the elemental sulfur and the compound which makes the composition alkaline are present in a weight ratio of not more than 1:1 and not less than 1:5.

5. The composition of claim 1 further comprising a binder, wherein the binder comprises a polymer comprising acid groups, and wherein the binder has an acid number of at least 7.

6. The chemical indicator composition of claim 1, wherein the chemical indicator composition further comprises a dye which causes the color of the composition in the presence of steam to become black; wherein without the dye, the color of the composition in the presence of steam would be brown.

7. The composition of claim 1, wherein the bismuth (III) compound is selected from the group consisting of bismuth subsalicylate, bismuth subgallate, bismuth acetate, bismuth citrate, bismuth neodecanoate, bismuth diethyldithiocarbamate, and combinations thereof.

8. The composition of claim 1, wherein the bismuth (III) compound is selected from the group consisting of bismuth subsalicylate, bismuth acetate, bismuth citrate, bismuth neodecanoate, and combinations thereof.

9. A chemical indicator composition comprising:
   a) a bismuth (III) compound;
   b) elemental sulfur;
   c) a compound which makes the composition alkaline when exposed to water vapor at an elevated temperature; and
   d) an acid selected from the group consisting of 2-hydroxybenzoic acid, benzoic acid, p-toluenesulfonic acid, phenylacetic acid, citric acid, phthalic acid, suberic acid, and combinations thereof, wherein the acid is present in an amount of at least 0.005 equivalents acid per equivalent of the compound which makes the composition alkaline.

10. The composition of claim 9, wherein the compound which makes the composition alkaline has a solubility in water at 100° C. of not more than 1 gram per 100 cubic centimeters of water.

11. A chemical indicator comprising:
   a substrate and the chemical indicator composition of claim 9 coated on at least a portion of a major surface of the substrate.

12. The indicator of claim 11, wherein the substrate is a paper with a pH of not more than 6.

13. A method of determining the effectiveness of a steam sterilization process, the method comprising:
   providing a chemical indicator of claim 11;
   placing the chemical indicator in a steam sterilization chamber;
   exposing the chemical indicator to steam at a temperature of at least 121° C.; and
   determining an optical density of the chemical indicator.

14. A method of determining effectiveness of a steam sterilization process, the method comprising determining whether or not sufficient removal of non-condensable gas from a steam sterilizer has occurred by:
   providing a chemical indicator according to claim 11, wherein the chemical indicator is positioned within a test pack; and wherein the chemical indicator composition of the chemical indicator is located at least in an area including the center of the test pack, at least in an area at or near the edges of the test pack, and at least in an area between the edges and center of the test pack;

positioning the test pack within the steam sterilizer;

exposing the test pack to the steam sterilization process; and examining the chemical indicator composition to determine the presence or absence of a first region distinctly lighter than a second surrounding region, the first region comprising a central zone and a peripheral zone surrounding the central zone and adjacent the second surrounding region; wherein both the central zone and the peripheral zone are distinctly lighter than the second surrounding region;

wherein the presence of the first region distinctly lighter than the second surrounding region is indicative of insufficient removal of non-condensable gas, and the absence of the first region distinctly lighter than the second surrounding region is indicative of sufficient removal of non-condensable gas.

15. The composition of claim 9, wherein the bismuth (III) compound and the elemental sulfur are present in a weight ratio of not more than 2:3 and not less than 0.5:3; and wherein the elemental sulfur and the compound which makes the composition alkaline are present in a weight ratio of not more than 1:1 and not less than 1:5.

16. A method of making a chemical indicator having a targeted change in optical density when exposed to a steam sterilization process condition; the method comprising:

selecting at least one optical density-controlling component for including in the chemical indicator; wherein the optical density-controlling component is selected from the acids: 2-hydroxybenzoic acid, benzoic acid, p-toluenesulfonic acid, phenylacetic acid, citric acid, phthalic acid, suberic acid, and combinations thereof;

preparing a chemical indicator composition comprising:
   a) a bismuth (III) compound;
   b) elemental sulfur;
   c) a compound which makes the composition alkaline when exposed to water vapor at an elevated temperature; and
   d) the at least one acid; and coating the composition on at least a portion of a major surface of a substrate.

17. The method of claim 16, wherein the at least one polymer comprising acid groups is selected.

18. The method of claim 16, wherein the compound which makes the composition alkaline has a solubility in water at 100° C. of not more than 1 gram per 100 cubic centimeters of water.

19. The method of claim 16, wherein the bismuth (III) compound and the elemental sulfur are present in the composition in a weight ratio of not more than 2:3 and not less than 0.5:3; and wherein the elemental sulfur and the compound which makes the composition alkaline are present in a weight ratio of not more than 1:1 and not less than 1:5.

* * * * *